United States Patent
Brown et al.

(10) Patent No.: US 6,548,671 B2
(45) Date of Patent: Apr. 15, 2003

(54) QUINOXALINYL AMIDE DERIVATIVES

(75) Inventors: Matthew F. Brown, Stonington, CT (US); Christopher S. Poss, N. Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/774,871

(22) Filed: Jan. 31, 2001

(65) Prior Publication Data

US 2002/0132810 A1 Sep. 19, 2002

Related U.S. Application Data

(60) Provisional application No. 60/180,159, filed on Feb. 4, 2000.

(51) Int. Cl.[7] ............... C07D 241/44; A61K 31/498
(52) U.S. Cl. ............................. 544/355; 514/249
(58) Field of Search .................. 544/355; 514/249

(56) References Cited

FOREIGN PATENT DOCUMENTS

| WO | WO 9305026 | | 3/1993 |
|---|---|---|---|
| WO | WO 98/38167 | * | 9/1998 |
| WO | WO 9940061 | | 8/1999 |

OTHER PUBLICATIONS

Thornber, Chemical Society Reviews, 8, pp. 563–580, 1979.*
Sato, et al., Blood, vol. 9, No. 1, Jan. 1, 1999, p 34–42.
Syehunie, et al., Blood, vol. 90, No. 4, Aug. 15, 1997, pp. 1379–1386.

* cited by examiner

*Primary Examiner*—Deepak Rao
(74) *Attorney, Agent, or Firm*—Peter C. Richardson; Gregg C. Benson; Lisa A. Samuels

(57) ABSTRACT

A compound of the formula

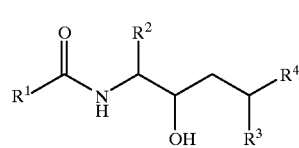

I or the pharmaceutically acceptable salt thereof; wherein $R^1$, $R^2$, $R^3$ and $R^4$ are as defined above useful to treat inflammation and other immune disorders.

24 Claims, No Drawings

QUINOXALINYL AMIDE DERIVATIVES

The present application claims the benefit of U.S. Provisional Application No. 60/180,159, filed Feb. 4, 2000.

BACKGROUND OF THE INVENTION

The present invention relates to novel hexanoic acid derivatives, methods of use and pharmaceutical compositions containing them.

The compounds of the invention are potent and selective inhibitors of MIP-1α binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokines shown to interact with CCR1 (e.g., RANTES and MCP-3)) induced chemotaxis of THP-1 cells and human leukocytes and are potentially useful for the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xenotransplantation, transplantation tissue rejection (chronic and acute), organ rejection (chronic and acute), atherosclerosis, restenosis, HIV infectivity (co-receptor usage), and granulomatous diseases (including sarcoidosis, leprosy and tuberculosis).

MIP-1α and RANTES are soluble chemotactic peptides (chemokines) which are produced by inflammatory cells, in particular CD8+ lymphocytes, polymorphonuclear leukocytes (PMNS) and macrophages, *J. Biol. Chem.*, 270 (30) 29671–29675 (1995). These chemokines act by inducing the migration and activation of key inflammatory and immuno-modulatory cells. Elevated levels of chemokines have been found in the synovial fluid of rheumatoid arthritis patients, chronic and rejecting tissue transplant patients and in the nasal secretions of allergic rhinitis patients following allergen exposure (Teran, et al., *J. Immunol.*, 1806–1812 (1996), and Kuna et al., *J. Allergy Clin. Immunol.* 321 (1994)). Antibodies which interfere with the chemokine/receptor interaction by neutralizing MIP1α or gene disruption have provided direct evidence for the role of MIP-1α and RANTES in disease by limiting the recruitment of monocytes and CD8+ lymphocytes (Smith et al., *J. Immunol,* 153, 4704 (1994) and Cook et al., *Science,* 269, 1583 (1995)). Together this data demonstrates that CCR1 antagonists would be an effective at treatment of several immune based diseases. The compounds described within are potent and selective antagonists of CCR1.

SUMMARY OF THE INVENTION

The present invention relates to compounds of the formula

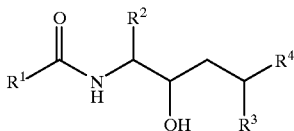

I or the pharmaceutically acceptable salt thereof; wherein $R^1$ is $(C_2-C_9)$heteroaryl optionally substituted with one or more substituents independently selected from the group consisting of hydrogen, deuterium, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C$=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alky$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

$R^2$ is phenyl-$(CH_2)_m$—, naphthyl-$(CH_2)_m$—, $(C_3-C_{10})$cycloalkyl-$(CH_2)_m$—, $(C_1-C_6)$alkyl or $(C_2-C_9)$heteroaryl-$(CH_2)_m$—, wherein m is an interger from zero to four; wherein each of said phenyl, naphthyl, $(C_3-C_{10})$cycloalkyl or $(C_2-C_9)$heteroaryl moieties of said phenyl-$(CH_2)_m$—, naphthyl-$(CH_2)_m$—, $(C_3-C_{10})$cycloalkyl-$(CH_2)_m$— or $(C_2-C_9)$heteroaryl-$(CH_2)_m$— groups may optionally be substituted with one or more substituents independently selected from hydrogen, deuterium, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C$=O)—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$ alkyl(C=O)—[N($C_1$–$C_6$)alkyl]($C_1$–$C_6$)alkyl, ($C_1$–$C_6$) alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, phenoxy, benzyloxy, ($C_3$–$C_{10}$)cycloalkyl, ($C_2$–$C_9$)heterocycloalkyl, and ($C_2$–$C_9$)heteroaryl;

$R^3$ is hydrogen, deuterium, ($C_1$–$C_{10}$)alkyl, ($C_3$–$C_{10}$)cycloalkyl-($CH_2$)$_n$—, ($C_2$–$C_9$)heterocycloalkyl-($CH_2$)$_n$—, ($C_2$–$C_9$)heteroaryl-($CH_2$)$_n$— or aryl-($CH_2$)$_n$—; wherein n is an interger from zero to six;

wherein said $R^3$ ($C_1$–$C_{10}$)alkyl group may optionally be substituted with one or more substituents, independently selected from hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C▽O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$-($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl; and wherein any of the carbon-carbon single bonds of said ($C_1$–$C_{10}$)alkyl may optionally be replaced by a carbon-carbon double bond;

wherein the ($C_3$–$C_{10}$)cycloalkyl moiety of said $R^3$ ($C_3$–$C_{10}$)cycloalkyl-($CH_2$)$_n$— group may optionally be substituted by one to three substitutents independently selected from the group consisting of hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl—(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$) alkyl(C=O)—[N($C_1$–$C_6$)alkyl]($C_1$–$C_6$)alkyl, ($C_1$–$C_6$) alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

wherein the ($C_2$–$C_9$)heterocycloalkyl moiety of said $R^3$ ($C_2$–$C_9$)heterocycloalkyl-($CH_2$)$_n$—group may contain from one to three heteroatoms independently selected from nitrogen, sulfur, oxygen, >S(=O), >$SO_2$ or >$NR^6$, wherein said ($C_2$–$C_9$)heterocycloalkyl moiety of said ($C_2$–$C_9$)heterocycloalkyl-($CH_2$)$_n$— group may optionally be substituted on any of the ring carbon atoms capable of forming an additional bond with a substituent independently selected from the group consisting of hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino ($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2N$—$SO_2$—, $H_2N$—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

wherein the ($C_2$–$C_9$)heteroaryl moiety of said $R^3$ ($C_2$–$C_9$)heteroaryl-($CH_2$)$_n$— group may contain from one to three heteroatoms independently selected from nitrogen, sulfur or oxygen wherein said ($C_2$–$C_9$)heteroaryl moiety of said ($C_2$–$C_9$)heteroaryl-($CH_2$)$_n$— group may optionally be substituted on any of the ring carbon atoms capable of forming an additional bond with a substituent selected from the group consisting of hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino ($C_1$–$C_6$)alkyl, $H_2N$—(C=O)—, ($C_1$–$C_6$)alkyl-NH—(C=O)—, [($C_1$–$C_6$)alkyl]$_2$N—(C=O)—, $H_2N$ (C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-SO$_2$—, ($C_1$–$C_6$)alkyl-SO$_2$—NH—, H$_2$N—SO$_2$—, H$_2$N—SO$_2$—($C_1$–$C_6$)alkyl, ($C_1$–$C_6$)alkylHN—SO$_2$—($C_1$–$C_6$)alkyl, [($C_1$–$C_6$)alkyl]$_2$N—SO$_2$—($C_1$–$C_6$)alkyl, CF$_3$SO$_3$—, ($C_1$–$C_6$)alkyl-SO$_3$—, phenyl, ($C_3$–$C_{10}$)cycloalkyl, ($C_2$–$C_9$)heterocycloalkyl, and ($C_2$–$C_9$)heteroaryl; and wherein said aryl moiety of said $R^3$ aryl-(CH$_2$)$_n$— group is optionally substituted phenyl or naphthyl, wherein said phenyl and naphthyl may optionally be substituted with from one to three substituents independently selected from the group consisting of hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, NO$_2$, amino, ($C_1$–$C_6$)alkylamino, [($C_1$–$C_6$)alkyl]$_2$amino, amino($C_1$–$C_6$)alkyl, ($C_1$–$C_6$)alkylamino ($C_1$–$C_6$)alkyl, [($C_1$–$C_6$)alkyl]$_2$amino($C_1$–$C_6$)alkyl, H$_2$N—(C=O)—, ($C_1$–$C_6$)alkyl-NH—(C=O)—, [($C_1$–$C_6$)alkyl]$_2$N—(C=O)—, H$_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-SO$_2$—, ($C_1$–$C_6$)alkyl-SO$_2$—NH—, H$_2$N—SO$_2$—, H$_2$N—SO$_2$—($C_1$–$C_6$)alkyl, ($C_1$–$C_6$)alkylHN—SO$_2$—($C_1$–$C_6$)alkyl, [($C_1$–$C_6$)alkyl]$_2$N—SO$_2$—($C_1$–$C_6$)alkyl, CF$_3$SO$_3$—, ($C_1$–$C_6$)alkyl-SO$_3$—, phenyl, ($C_3$–$C_{10}$)cycloalkyl, ($C_2$–$C_9$)heterocycloalkyl, and ($C_2$–$C_9$)heteroaryl;

or $R^3$ and the carbon to which it is attached form a five to seven membered carbocyclic ring, wherein any of the carbon atoms of said five membered carbocyclic ring may optionally be substituted with a substituent selected from the group consisting of hydrogen, deuterium, halo, CN, ($C_1$–$C_6$)alkyl optionally substituted with one or more fluorine atoms (preferably one to three fluorine atoms), hydroxy, hydroxy-($C_1$–$C_6$)alkyl, ($C_1$–$C_6$)alkoxy optionally substituted with one or more fluorine atoms (preferably one to three fluorine atoms), ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, NO$_2$, amino, ($C_1$–$C_6$)alkylamino, [($C_1$–$C_6$)alkyl]$_2$amino, amino($C_1$–$C_6$)alkyl, ($C_1$–$C_6$)alkylamino($C_1$–$C_6$)alkyl, [($C_1$–$C_6$)alkyl]$_2$amino($C_1$–$C_6$)alkyl, H$_2$N—(C=O)—, ($C_1$–$C_6$)alkyl-NH—(C=O)—, [($C_1$–$C_6$)alkyl]$_2$N—(C=O)—, H$_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-SO$_2$—, ($C_1$–$C_6$)alkyl-SO$_2$—NH—, H$_2$N—SO$_2$—, H$_2$N—SO$_2$—($C_1$–$C_6$)alkyl, ($C_1$–$C_6$)alkylHN—SO$_2$—($C_1$–$C_6$)alkyl, [($C_1$–$C_6$)alkyl]$_2$N—SO$_2$—($C_1$–$C_6$)alkyl, CF$_3$SO$_3$—, ($C_1$–$C_6$)alkyl-SO$_3$—, phenyl, ($C_3$–$C_{10}$)cycloalkyl, ($C_2$–$C_9$)heterocycloalkyl, and ($C_2$–$C_9$)heteroaryl; wherein one of the carbon-carbon bonds of said five to seven membered carbocyclic ring may optionally be fused to an optionally substituted phenyl ring, wherein said substitutents may be independently selected from hydrogen, deuterium, halo, CN, ($C_1$–$C_6$)alkyl optionally substituted with one or more fluorine atoms (preferably one to three fluorine atoms), hydroxy, hydroxy-($C_1$–$C_8$)alkyl, ($C_1$–$C_6$)alkoxy optionally substituted with one or more fluorine atoms (preferably one to three fluorine atoms), ($C_1$–$C_6$)alkoxy ($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, NO$_2$, amino, ($C_1$–$C_6$)alkylamino, [($C_1$–$C_6$)alkyl]$_2$amino, amino($C_1$–$C_6$)alkyl, ($C_1$–$C_6$)alkylamino ($C_1$–$C_6$)alkyl, [($C_1$–$C_6$)alkyl]$_2$amino($C_1$–$C_6$)alkyl, H$_2$N—(C=O)—, ($C_1$–$C_6$)alkyl-NH—(C=O)—, [($C_1$–$C_6$)alkyl]$_2$N—(C=O)—, H$_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl(C=O)—[N($C_1$–$C_6$)alkyl]($C_1$–$C_6$)alkyl, ($C_1$–$C_6$)alkyl-S—, ($C_1$–$C_6$)alkyl-(S=O)—, ($C_1$–$C_6$)alkyl-SO$_2$—, ($C_1$–$C_6$)alkyl-SO$_2$—NH—, H$_2$N—SO$_2$—, H$_2$N—SO$_2$—($C_1$–$C_6$)alkyl, ($C_1$–$C_6$)alkylHN—SO$_2$—($C_1$–$C_6$)alkyl, [($C_1$–$C_6$)alkyl]$_2$N—SO$_2$—($C_1$–$C_6$)alkyl, CF$_3$SO$_3$—, ($C_1$–$C_6$)alkyl-SO$_3$—, phenyl, ($C_3$–$C_{10}$)cycloalkyl, ($C_2$–$C_9$)heterocycloalkyl, and ($C_2$–$C_9$)heteroaryl; and $R^4$ is ($C_2$–$C_9$)heteroaryl, ($C_2$–$C_9$)heterocycloalkyl, $R^5R^6$N-sulfonyl or a group of the formula

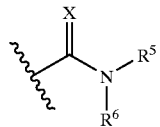

wherein $R^5$ is hydrogen, deuterium, ($C_1$–$C_6$)alkyl, hydroxy, ($C_1$–$C_6$)alkoxy, hydroxy($C_1$–$C_6$)alkyl, ($C_1$–$C_6$)alkoxy (C=O)—, ($C_3$–$C_{10}$)cycloalkyl-(CH$_2$)$_p$—, ($C_2$–$C_9$)heterocycloalkyl-(CH$_2$)$_p$—, ($C_2$–$C_9$)heteroaryl-(CH$_2$)$_p$—, phenyl-(CH$_2$)$_p$—, or naphthyl-(CH$_2$)$_p$—, wherein p is an integer from zero to four; wherein said ($C_2$–$C_9$)heterocycloalkyl, ($C_2$–$C_9$)heteroaryl, phenyl and naphthyl groups of said ($C_2$–$C_9$)heterocycloalkyl-(CH$_2$)$_p$—, ($C_2$–$C_9$)heteroaryl-(CH$_2$)$_p$—, phenyl-(CH$_2$)$_p$—, or naphthyl-(CH$_2$)$_p$— may be optionally substituted on any of the ring atoms capable of supporting an additional bond with a substituent selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)

alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$)alkyl, H(O=C)—, H(O=C)—($C_1$–$C_8$)alkyl, ($C_1$–$C_6$) alkyl (O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$ amino, amino ($C_1$–$C_6$)alkyl, ($C_1$–$C_6$)alkylamino ($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_8$)alkyl]$_2$N—(C=O)—, $H_2$N(C=O)—($C_1$–$C_6$)alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$)alkyl (C=O)—[N($C_1$–$C_6$)alkyl]($C_1$–$C_6$)alkyl, ($C_1$–$C_6$)alkyl-S—, ($C_1$–$C_8$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$)cycloalkyl, ($C_2$–$C_9$)heterocycloalkyl, and ($C_2$–$C_9$)heteroaryl;

or $R^5$ and $R^6$ together with the nitrogen atom to which they are attached form a ($C_2$–$C_9$)heterocycloalkyl group wherein any of the ring atoms of said ($C_2$–$C_9$) heterocycloalkyl group may optionally be substituted with a substituent selected from the group consisting of hydrogen, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$) alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$) alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$) alkyl, H(O=C)—, H(O=C)—($C_1$–$C_6$)alkyl, ($C_1$–$C_6$) alkyl(O=C)—, ($C_1$–$C_6$)alkyl(O=C)—($C_1$–$C_6$)alkyl, $NO_2$, amino, ($C_1$–$C_6$)alkylamino, [($C_1$–$C_6$)alkyl]$_2$ amino, amino($C_1$–$C_6$)alkyl, ($C_1$–$C_6$)alkylamino ($C_1$–$C_6$)alkyl, [($C_1$–$C_6$)alkyl]$_2$amino($C_1$–$C_6$)alkyl, $H_2$N—(C=O)—, ($C_1$–$C_6$)alkyl-NH—(C=O)—, [($C_1$–$C_6$)alkyl]$_2$N—(C=O)—, $H_2$N(C=O)—($C_1$–$C_6$) alkyl, ($C_1$–$C_6$)alkyl-HN(C=O)—($C_1$–$C_6$)alkyl, [($C_1$–$C_6$)alkyl]$_2$N—(C=O)—($C_1$–$C_6$)alkyl, H(O=C)—NH—, ($C_1$–$C_6$)alkyl(C=O)—NH, ($C_1$–$C_6$)alkyl(C=O)—[NH]($C_1$–$C_6$)alkyl, ($C_1$–$C_6$) alkyl(C=O)—[N($C_1$–$C_6$)alkyl]($C_1$–$C_6$)alkyl, ($C_1$–$C_6$) alkyl-S—, ($C_1$–$C_6$)alkyl-(S=O)—, ($C_1$–$C_6$)alkyl-$SO_2$—, ($C_1$–$C_6$)alkyl-$SO_2$—NH—, $H_2$N—$SO_2$—, $H_2$N—$SO_2$—($C_1$–$C_6$)alkyl, ($C_1$–$C_6$)alkylHN—$SO_2$—($C_1$–$C_6$)alkyl, [($C_1$–$C_6$)alkyl]$_2$N—$SO_2$—($C_1$–$C_6$)alkyl, $CF_3SO_3$—, ($C_1$–$C_6$)alkyl-$SO_3$—, phenyl, ($C_3$–$C_{10}$) cycloalkyl, ($C_2$–$C_9$)heterocycloalkyl, and ($C_2$–$C_9$) heteroaryl;

$R^6$ is hydrogen, deuterium, ($C_1$–$C_6$)alkyl or amino;

X is $NR^7$ or S wherein $R^7$ is defined as $R^4$ above; and with the proviso that when $R^4$ is a five-membered heterocyclic group, either $R^2$ or $R^3$ must be substituted by a functional group other than ($C_1$–$C_6$)alkyl, hydroxy ($C_1$–$C_6$)alkyl, ($C_1$–$C_6$)alkoxy, ($C_1$–$C_6$)alkyl-(C=O)—O—, ($C_1$–$C_6$)alkyl-(C=O)—O—($C_1$–$C_6$)alkyl, amino, ($C_1$–$C_6$)alkylamino, [($C_1$–$C_6$)alkyl]$_2$amino, amino($C_1$–$C_6$)alkyl, benzofuryl, indolyl, azacycloalkyl, azabicycloalkyl or benzopiperidinyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3- naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention may contain olefin-like double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

($C_3$–$C_{10}$)Cycloalkyl when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl etc.

($C_2$–$C_9$)Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$–$C_9$)heterocycloalkyl rings is through a carbon or a $sp^3$ hybridized nitrogen heteroatom.

($C_2$–$C_9$)Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$–$C_9$)

heterocycloalkyl rings is through a carbon atom or a sp³ hybridized nitrogen heteroatom.

Aryl when used herein refers to phenyl or naphthyl.

The compounds of this invention include all conformational isomers (e.g., cis and trans isomers) and all optical isomers of compounds of the formula I (e.g., enantiomers and diastereomers), as well as racemic, diastereomeric and other mixtures of such isomers.

Preferred compounds of the of formula I include those with the stereochemistry depicted in formula Ia

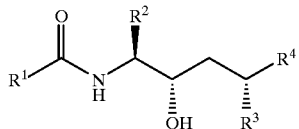

Preferred compounds of the formula I include those wherein $R^1$ is optionally substituted pyrazolo[3,4-b]pyridinyl, cinnolinyl, pyridinyl, 6,7-dihydro-5H-[1]pyrindinyl, benzothiazolyl, indolyl, pyrazinyl, benzoimidazolyl, benzofuranyl, benzo[b]thiophenyl, naphthalenyl, quinoxalinyl, isoquinolinyl, 5,6,7,8-tetrahydro-quinolin-3-yl or quinolinyl, more preferably pyrazolo[3,4-b]pyridin-5-yl, cinnolin-4-yl, pyridin-2-yl, 6,7-dihydro-5H-[1]pyrindin-3-yl, benzothiazol-2-yl, indol-2-yl, pyrazin-2-yl, benzoimidazol-2-yl, benzofuran-2-yl, benzo[b]thiophen-2-yl, naphthalen-2-yl, quinoxalin-2-yl, quinoxalin-6-yl, isoquinolin-1-yl, isoquinolin-3-yl, isoquinolin-4-yl, 5,6,7,8-tetrahydro-quinolin-3-yl, quinolin-2-yl, quinolin-3-yl, quinolin-4-yl or quinolin-6-yl, most preferably quinoxalin-6-yl, quinolin-2-yl, quinolin-3-yl, quinoxalin-2-yl, quinolin-4-yl or quinolin-6-yl.

Other preferred compounds of formula I include those wherein $R^2$ is optionally substituted phenyl, benzyl, naphthyl, cyclohexyl, thienyl, thiazolyl, pyridyl, oxazolyl, furanyl, or thiophenyl; wherein said substituents are independently selected from hydrogen, halo, $(C_1-C_6)$alkyl, trifluoromethyl, trifluoromethoxy, hydroxy, —C(=O)—OH, $(C_1-C_6)$alkoxy, $(C_1-C_6)$alkoxy(C=O)—, $NO_2$, amino, $(C_1-C_6)$alkylamino, $[(C_1-C_6)$alkyl$]_2$amino, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, $H_2N$—(C=O)—, $(C_1-C_6)$alkyl-NH—(C=O)—, $[(C_1-C_6)$alkyl$]_2$N—(C=O)—, $H_2N$(C=O)—$(C_1-C_6)$alkyl, $(C_1-C_6)$alkyl-HN(C=O)—$(C_1-C_6)$alkyl, $[(C_1-C_6)$alkyl$]_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N($C_1-C_6$)alkyl]$(C_1-C_6)$alkyl, phenoxy, and benzyloxy.

Other preferred compounds of formula I include those wherein $R^3$ is optionally substituted $(C_1-C_{10})$alkyl, benzyl, pyranyl or $(C_3-C_{10})$cycloalkyl-$(CH_2)_n$—, wherein any of the carbon—carbon single bonds of said $(C_1-C_{10})$alkyl may be optionally replaced by a carbon—carbon double bond; more preferably optionally substituted n-butyl, isobutyl, n-pentyl, 3-methyl-butyl, 2-methyl-pentyl, allyl, cyclopentyl, cyclohexyl or cycloheptyl, more preferably wherein the substituent is fluoro, $(C_1-C_6)$alkyl or hydroxy.

Examples of specific preferred compounds of the formula I are the following:

Quinoxaline-2-carboxylic acid [1(S)-(3-fluoro-benzyl)-2(S),7-dihydroxy-4(R)-(1H-imidazol-2-yl)-7-methyl-octyl]-amide;

Quinoxaline-2-carboxylic acid [1(S)-benzyl-2(S),7-dihydroxy-4(R)-(1H-imidazol-2-yl)-7-methyl-octyl]-amide;

Quinoxaline-2-carboxylic acid [7-fluoro-1(S)-(3-fluoro-benzyl)-2(S)-hydroxy-4(R)-(1H-imidazol-2-yl)-7-methyl-octyl]-amide;

Quinoxaline-2-carboxylic acid [1(S)-benzyl-7-fluoro-2(S)-hydroxy-4(R)-(1H-imidazol-2-yl)-7-methyl-octyl]-amide;

Quinoxaline-2-carboxylic acid [1(S)-(3-fluoro-benzyl)-2(S),7-dihydroxy-7-methyl-4(R)-sulfamoyl-octyl]-amide;

Quinoxaline-2-carboxylic acid (1(S)-benzyl-2(S),7-dihydroxy-7-methyl-4(R)-sulfamoyl-octyl)-amide;

Quinoxaline-2-carboxylic acid [7-fluoro-1(S)-(3-fluoro-benzyl)-2(S),-hydroxy-7-methyl-4(R)-sulfamoyl-octyl]-amide;

Quinoxaline-2-carboxylic acid (1(S)-benzyl-7-fluoro-2(S)-hydroxy-7-methyl-4(R)-sulfamoyl-octyl)-amide;

Quinoxaline-2-carboxylic acid [1(S)-(3-fluoro-benzyl)-(2(S),7-dihydroxy-7-methyl-4(R)-methylsulfamoyl-octyl]-amide;

Quinoxaline-2-carboxylic acid (1(S)-benzyl-2(S)-7-dihydroxy-7-methyl-4(R)-methylsulfamoyl-octyl)-amide;

Quinoxaline-2-carboxylic acid [(S)-(3-fluoro-benzyl)-2(S),7-hydroxy-7-methyl-4(R)-methylsulfamoyl-octyl]-amide;

Quinoxaline-2-carboxylic acid [I(S)-benzyl-7-fluoro-2(S)-hydroxy-7-methyl-4(R)-methylsulfamoyl-octyl]-amide;

Quinoxaline-2-carboxylic acid [4(R)-(4-chloro-1 H-imidazol-2-yl )-1 (S)-(3-fluoro-benzyl)-2(S),-7-fluoro-benzyl)-2(S)-hydroxy-dihydroxy-7-methyl-octyl]-amide;

Quinoxaline-2-carboxylic acid [1(S)-benzyl-4(R)(4-chloro-1H-imidazol-2-yl)-2(S),-7-hydroxy-7-methyl-octyl]-amide;

Quinoxaline-2-carboxylic acid [4(R)-(4-chloro-1H-imidazol-2-yl)-7-fluoro-1(S)-(3-fluoro-benzyl)-2(S)-hydroxy-7-methyl-octyl]-amide;

Quinoxaline-2-carboxylic acid [1(S)-benzyl-4(R)(4-chloro-1H-imidazol-2-yl)-7-fluoro-2(S)-hydroxy-7-methyl-octyl]-amide;

Quinoxaline-2-carboxylic acid [1(S)-(3-fluoro-benzyl)-4(R)-(4-fluoro-1H-imidazol-2-yl)-2(S),7-dihydroxy-7-methyl-octyl]-amide;

Quinoxaline-2-carboxylic acid [1(S)-benzyl-4(R)-(4-fluoro-1H-imidazol-2-yl)-2(S)-7-dihydroxy-7-methyl-octyl]amide;

Quinoxaline-2-carboxylic acid [7-fluoro-1(S)-(3-fluoro-benzyl)-4(R)-(4-fluoro-1H-imidazol-2-yl)-2(S)-hydroxy-7-methyl-octyl]-amide; and Quinoxaline-2-carboxylic acid [1(S)-benzyl-7-fluoro-4(R)-(4-fluoro-1H-imidazol-2-yl)-2(S)-hydroxy-7-methyl-octyl]amide.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xeno-transplantation, transplantation tissue rejection, atherosclerosis, restenosis, HIV infectivity (co-receptor usage), and granulomatous diseases (including sarcoidosis, leprosy and tuberculosis). in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by inhibiting MIP-1α binding to the receptor CCR1 in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xeno-transplantation, transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by antagonizing the CCR1 receptor in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xeno-transplantation, transplantation tissue rejection, atherosclerosis, restenosis, HIV infectivity (co-receptor usage), and granulomatous diseases (including sarcoidosis, leprosy and tuberculosis) in a mammal, preferably a human, comprising a CCR1 receptor antagonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by antagonizing the CCR1 receptor in a mammal, preferably a human, comprising a CCR1 receptor antagonizing effective amount of a compound of the formula I, or a pharmaceutically acceptable salt thereof, and a pharmaceutically acceptable carrier.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xeno-transplantation, transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention a CCR1 receptor antagonizing effective amount of a compound of formula I, or a pharmaceutically acceptable salt thereof.

DETAILED DESCRIPTION OF THE INVENTION

The following reaction Schemes illustrate the preparation of the compounds of the present invention. Unless otherwise indicated $R^1$, $R^2$, $R^3$ and $R^4$ in the reaction Schemes and the discussion that follow are defined as above.

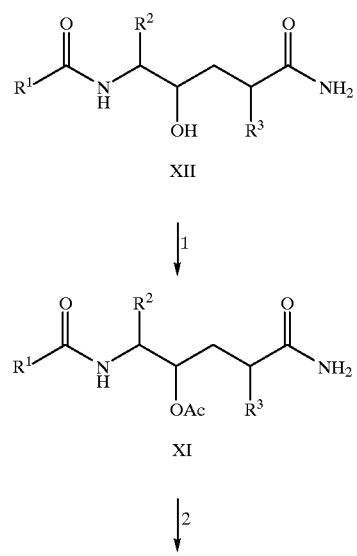

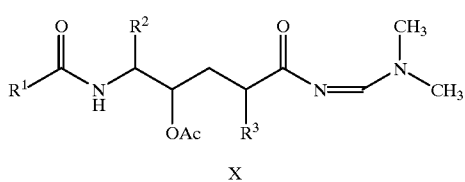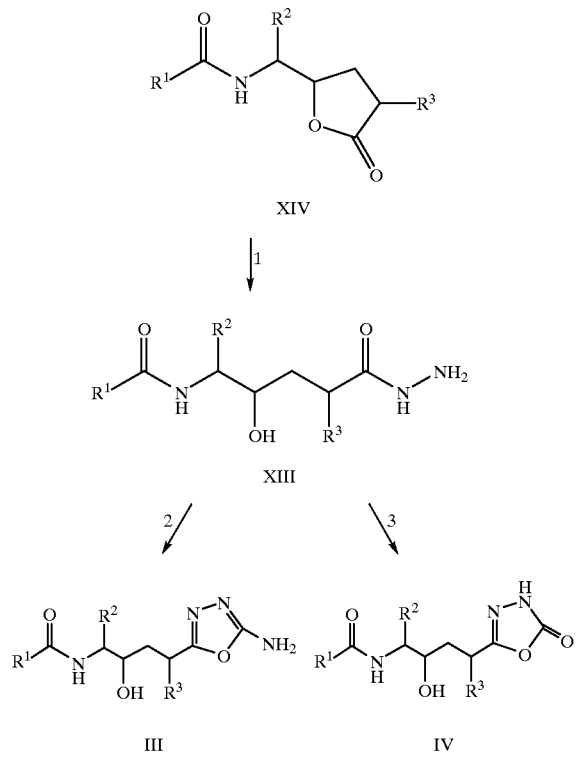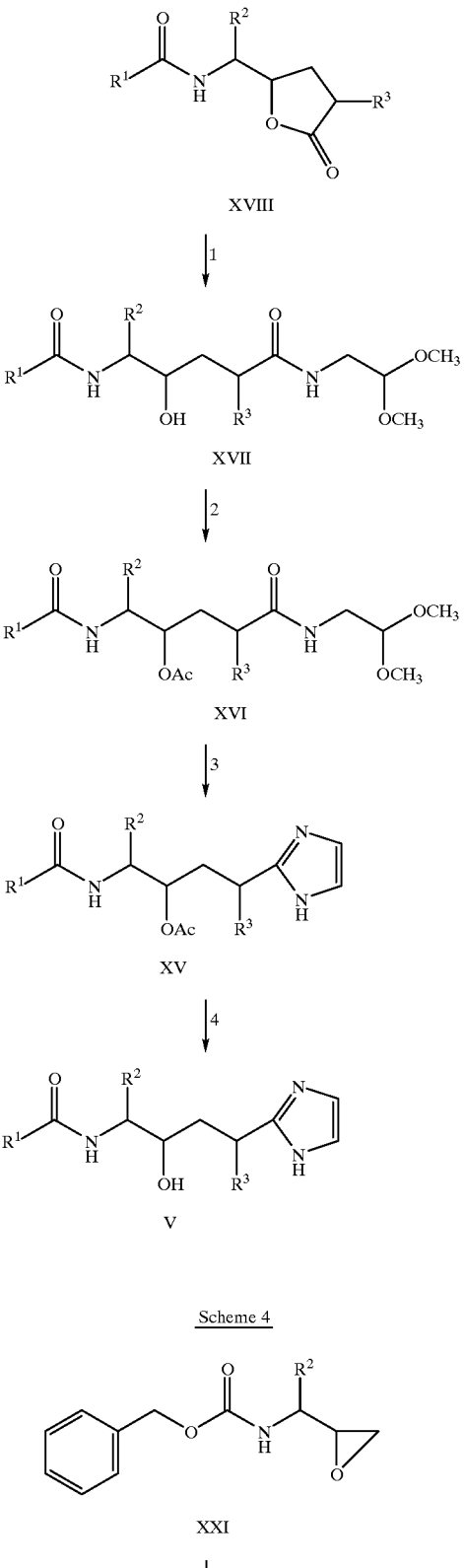

-continued
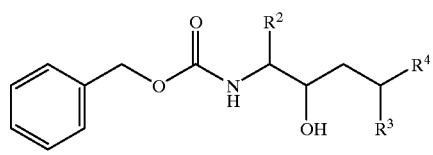
XX
↓2
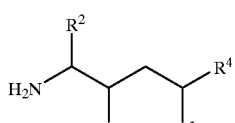
XIX
↓3
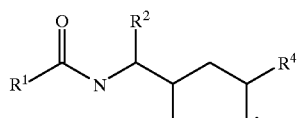
I
-continued
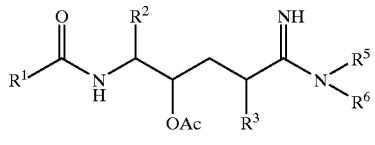
XXIII
↓4
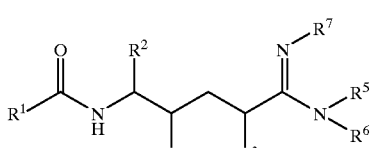
XXII
↓5
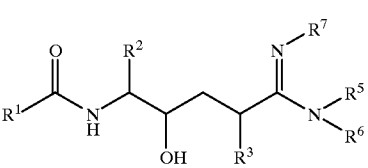
VI
Scheme 5
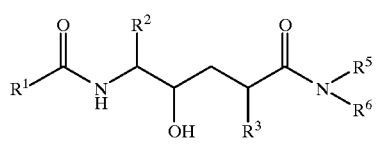
XXIV
↓1
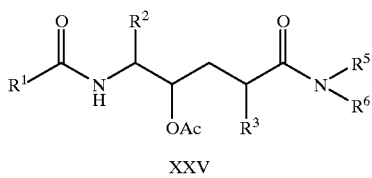
XXV
↓2
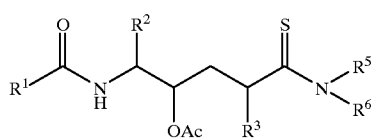
XXIV
↓3
Scheme 6
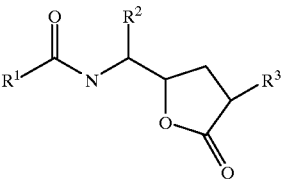
XXXII
↓1
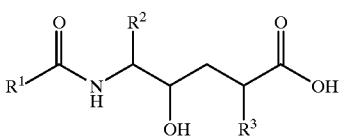
XXXI
↓2

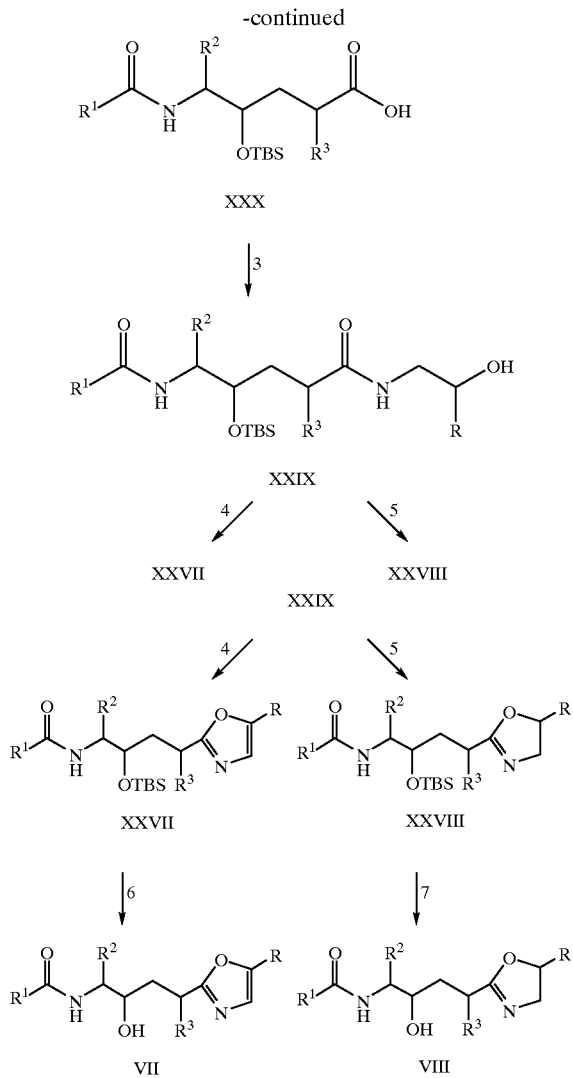

Compounds of formula I may be prepared by methods described in WO 98/38167, which is incorporated by reference in its entirety.

In reaction 1 of Scheme 1, the alcohol compound of formula XII is converted to the corresponding acetate compound of formula XI by reacting XII with acetic anhydride in the presence of 4-dimethylaminopyridine (DMAP) and pyridine. The reaction 1 stirred at a temperature between about 0° C. to about room temperature, preferably about 0° C., for a time period between about 1 hour to about 3 hours, preferably about 2 hours.

In reaction 2 of Scheme 1, the compound of formula XI is converted to the corresponding compound of formula X by reacting XI with N,N-dimethylformamide dimethyl acetal in the presence of a polar protic solvent, such as methanol. The reaction is stirred at a temperature between about 40° C. to about 60° C., preferably about 50° C., for a time period between about 30 minutes to about 2 hours, preferably about 1 hour.

In reaction 3 of Scheme 1, the compound of formula X is converted to the corresponding triazole compound of formula IX by reacting X with hydrazine in the presence of acetic acid. The reaction is stirred at a temperature between about 40° C. to about 60° C., preferably about 50° C., for a time period between about 30 minutes to about 2 hours, preferably about 1 hour.

In reaction 4 of Scheme 1, the compound of formula IX is converted to the corresponding compound of formula II by deprotecting IX with potassium carbonate in the presence of methanol at room temperature overnight.

In reaction 1 of Scheme 2, the lactone compound of formula XIV is converted to the corresponding hydrazide compound of formula XII by reacting XIV with hydrazine in a polar protic solvent, such as methanol. The reaction is stirred at room temperature overnight.

In reaction 2 of Scheme 2, the hydrazine compound of formula XIII is converted to the corresponding 1,2,4-oxadiazole compound of formula III by reacting XIII with cyanogen bromide in the presence of dioxane and water. The reaction is heated to reflux for a time period between about 30 minutes to about 2 hours, preferably about 1 hour.

In reaction 3 of Scheme 2, the hydrazide compound of formula XIII is converted to the corresponding compound of formula IV by reacting XIII with CDI in the presence of a base, such as triethylamine, and a polar aprotic solvent, such as tetrahydrofuran. The reaction is stirred at room temperature for a time period between about 10 hours to about 20 hours, preferably overnight.

In reaction 1 of Scheme 3, the lactone compound of formula XVIII is converted to the corresponding compound of formula XVII by reacting XVIII with aminoacetaldehyde dimethyl acetal in the presence of dioxane. The reaction is stirred overnight at a temperature between about 30° C. to about 70° C., preferably about 50° C.

In reaction 2 of Scheme 3, the alcohol compound of formula XVII is converted to the corresponding acetate compound of formula XVI according to the procedure described above in reaction 1 of Scheme 1.

In reaction 3 of Scheme 3, the compound of formula XVI is converted to the corresponding imidazole compound of formula XV by reacting XVI with ammonium acetate in the presence of acetic acid. The reaction is stirred at a temperature between about 105° C. to about 125° C., preferably about 115° C., for a time period between about 3 hours to about 5 hours, preferably about 4 hours.

In reaction 4 of Scheme 3, the compound of formula XV is converted to the corresponding compound of formula V according to the procedure described above in reaction 4 of Scheme 1.

In reaction 1 of Scheme 4, the epoxide compound of formula XXI is converted to the corresponding compound of formula XX by reacting XXI with a compound of the formula, $CHR^3R^4$, in the presence of a base, such as n-butyllithium, and a polar aprotic solvent, such as tetrahydrofuran. The reaction is carried out at a temperature between about −78° C. to about 0° C., preferably about −78° C., for a time period between about 1 hours to about 4 hours, preferably about 2 hours.

In reaction 2 of Scheme 4, the compound of formula XX is converted to the corresponding compound of formula XIX by removal of the carbobenzyloxy protecting group through hydrogenation of XX in the presence of palladium on carbon and a polar protic solvent, such as ethanol. The reaction is carried out at a temperature between about 0° C. to room temperature, preferably room temperature, for a time period between about 1 hour to about 24 hours, preferably about 15 hours.

In reaction 3 of Scheme 4, the compound of formula XIX is converted to the corresponding compound of formula I by reacting XIX with a compound of the formula, $R^1$—CO—Cl, in the presence of a base, such as triethylamine, and a polar aprotic solvent, such as methylene chloride. The reaction is carried out at a temperature between about −20° C. to about 40° C., preferably about 0° C., for a time period between about 1 hour to about 24 hours, preferably about 2 hours.

In reaction 1 of Scheme 5, the compound of formula XXVI is converted to the corresponding compound of formula XXV according to the procedure described above in reaction 1 of Scheme 1.

In reaction 2 of Scheme 5, the amide compound of formula XXV is converted to the thioacetamide compound of formula XXIV by reacting XXV with Lawesson's Reagent, [2,4-bis(4-methoxyphenyl)-1,3-dithia-2,4-diphosphetane-2,4-disulfide], in the presence of a polar aprotic solvent, such as tetrahydrofuran. The reaction is carried out at a temperature between about 0° C. to about 60° C., preferably about 25 ° C, for a time period between about 1 hour to about 24 hours, preferably about 5 hours.

In reaction 3 of Scheme 5, the thioacetamide compound of formula XXIV is converted to the corresponding compound of formula XXIII by first treating XXIV with methyl iodide, followed by reacting the compound so formed with ammonia in methyl alcohol. The reaction is carried out at a temperature between about 0° C. to about 60° C., preferably about 25° C., for a time period between about 1 hour to about 24 hours, preferably about 15 hours.

In reaction 4 of Scheme 5, the compound of formula XXIII is converted to the corresponding compound of formula XXII by reacting XXII with (a) $R^8$ sulfonyl chloride when $R^7$ is $R^8S(O)_2$; (b) cyanogen bromide when $R^7$ is cyano; (c) L—N=C=O when $R^7$ is an amide and L is a leaving group; or (d) an acyl chloride compound of the formula, $R^8$—CO—Cl, when $R^7$ is $R^8C(O)$.

In reaction 5 of Scheme 5, the compound of formula XXII is converted to the corresponding compound of formula VI according to the procedure described above in reaction 1 of Scheme 1.

In reaction 1 of Scheme 6, the lactone of formula XXXII is converted to the corresponding compound of formula XXXI by reacting XXXII with a base, such as lithium hydroxide, in the presence of a mixture of water and a polar aprotic solvent, such as tetrahydrofuran. The reaction is carried out at a temperature between about 0° C. to about 60° C., preferably about 25° C., for a time period between about 1 hour to about 24 hours, preferably about 2 hours.

In reaction 2 of Scheme 6, the compound of formula XXXI is converted to the corresponding compound of formula XXX by reacting XXXI with tert-butyldimethylsilyl chloride in the presence of imidazole and polar protic solvent, such as dimethylformamide. The reaction is carried out at a temperature between about 0° C. to about 60° C., preferably about 25° C., for a time period between about 1 day to 7 days, preferably 1 day.

In reaction 3 of Scheme 6, the compound of formula XXX is converted to the corresponding compound of formula XXIX by reacting XXX with a compound of the formula

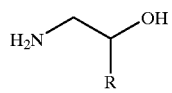

in the presence of 1-hydroxybenzotriazole hydrate, 1-(3-dimethylaminopropyl)-3-ethylcarbodiimide and a polar aprotic solvent, such as methylene chloride. The reaction is carried out at a temperature between about 0° C. to about 30° C., preferably about 25° C., for a time period between about 1 hour to about 24 hours, preferably about 25 hours.

In reaction 4 of Scheme 6, the compound of formula XXIX is converted to the corresponding oxazole compound of the formula XXVII by first oxidizing XXIX with the Dess-Martin periodinane oxidation reagent of the formula

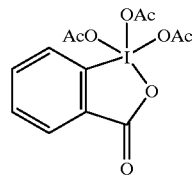

followed by treating the compound so formed with triphenylphosphine, triethylamine, hexachloroethane and a polar aprotic solvent, such as methylene chloride. The reaction is carried out at a temperature between about 0° C. to about 40° C., preferably about 25° C., for a time period between about 5 hours to about 24 hours, preferably about 15 hours.

In reaction 5 of Scheme 6, the compound of formula XXIX is converted to the corresponding oxazoline compound of formula XXVIII by treating XXIX with triphenylphosphine, hexachloroethane, triethylamine and a polar aprotic solvent, such as methylene chloride. The reaction is carried out at a temperature between about 0° C. to about 40° C., preferably about 25° C., for a time period between about 5 hours to about 24 hours, preferably about 15 hours.

In reaction 6 of Scheme 6, the compound of formula XXVII is converted to the corresponding compound of formula VII by treating XXVII with tert-butyl ammonium fluoride. The reaction is carried out at a temperature between about 0° C. to about 40° C., preferably about 25° C., for a time period between about 1 hour to about 24 hours, preferably about 2 hours.

In reaction 7 of Scheme 6, the compound of formula XXVIII is converted to the corresponding compound of formula VIII according to the procedure described above in reaction 6 of Scheme 6.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptors. The active compounds are useful in the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), chronic bronchitis, xenotransplantation, transplantation tissue rejection, atherosclerosis, restenosis, HIV infectivity (co-receptor usage), and granulomatous diseases (including sarcoidosis, leprosy and tuberculosis).

The activity of the compounds of the invention can be assessed according to procedures know to those of ordinary skill in the art. Examples of recognized methods for determining CCR1 induced migration can be found in Coligan, J. E., Kruisbeek, A. M., Margulies, D. H., Shevach, E. M., Strober, W. editors: *Current Protocols In Immunology*, 6.12.1–6.12.3. (John Wiley and Sons, New York, 1991). One specific example of how to determine the activity of a compound for inhibiting migration is described in detail below.

Chemotaxis Assay

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/ml of bovine serum albumin. Briefly, MIP-1α (Peprotech, Inc., P.O. Box 275, Rocky Hill N.J.) or other test agonists, were placed into the lower chambers of the Boyden chamber. A polycarbonate filter was then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention that were tested had $IC_{50}$ of less than 25 μM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 μg to 1000 μg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with other therapeutic agents such as with T-cell immunosuppressant agents such as cyclosporin A and FK-506, with steroid sparing agents such as Cellcept®, or with classical anti-inflammatory agents (e.g. cyclooxygenase/lipoxegenase inhibitors) such as tenidap, aspirin, acetaminophen, naproxen and piroxicam.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C. All non-aqueous reactions were run under a nitrogen atmosphere for convenience and to maximize yields. Concentration at reduced pressure means that a rotary evaporator was used. The names for the compounds of the invention were created by the Autonom 2.0 PC-batch version from Beilstein Informationssysteme GmbH (ISBN 3-89536-976-4).

EXAMPLE 1

Quinoxaline-2-carboxylic acid [1-(3-fluoro-benzyl)-2,7-dihydroxy-4-(1H-imidazol-2-yl)-7-methyl-octyl]-amide To a solution of trifluoro-acetic acid 3-(5-{2-(3-fluoro-phenyl)-1-[(quinoxaline-2-carbonyl)-amino]-ethyl}-2-oxo-tetrahydro-furan-3-yl)-1,1-dimethyl-propyl ester (212 mg, 0.378 mmol) in methanol (4 mL) was added aminoacetaldehyde dimethyl acetal (0.375 mL, 3.44 mM) and stirred for 14 days. The reaction was concentrated to provide the crude product which was purified by silica get chromatography to yield the title compound (197 mg, 91%).

Acetic acid 3-(2,2-dimethoxy-ethylcarbamoyl)-1-{2-(3-fluoro-phenyl)-1-[(quinoxaline-2-carbonyl)-amino]-ethyl}-6-hydroxy-6-methyl-heptyl ester To a solution of quinoxaline-2-carboxylic acid [4-(2,2-dimethoxy-ethylcarbamoyl)-1-(3-fluoro-benzyl)-2,7-dihydroxy-7-methyl-octyl]-amide (192 mg, 0.336 mmol) in pyridine (0.6 mL) was added dimethylaminopyridine (DMAP) (10 mg, 0.082 mmol) and acetic anhydride (0.093 mL, 0.984 mmol). The resulting solution was stirred for 3 hours then diluted with methylene chloride and washed with 1 M hydrochloric acid. The organic layer was dried over sodium sulfate, filtered and concentrated to give the title compound as a white foam (198 mg, 96%).

Acetic acid 1-{2-(3-fluoro-phenyl)-1-[(quinoxaline-2-carbonyl)-amino]-ethyl}-6-hydroxy-3-(1H-imidazol-2-yl)-6-methyl-heptyl ester To a solution of acetic acid 3-(2,2-dimethoxy-ethylcarbamoyl)-1-{2-(3-fluoro-phenyl)-1-[(quinoxaline-2-carbonyl)-amino]-ethyl}-6-hydroxy-6-methyl-heptyl ester (150 mg, 0.245 mmol) in acetic acid (2 mL) was added ammonium acetate (1.5 g 19.5 mmol). The resulting mixture was heated to 115° C. for 3 hours, cooled to ambient temperature and diluted with ethyl acetate. The solution was then neutralized with saturated aqueous sodium bicarbonate. The organic layer was dried over sodium sulfate, filtered and concentrated. Chromatography on silica gel gave the title compound (22.5 mg, 17%).

Quinoxaline-2-carboxylic acid [1-(3-fluoro-benzyl)-2,7-dihydroxy-4-(1H-imidazol-2-yl)-7-methyl-octyl]-amide To a solution of acetic acid 1-{2-(3-fluoro-phenyl)-1-[(quinoxaline-2-carbonyl)-amino]-ethyl}-6-hydroxy-3-(1H-imidazol-2-yl)-6-methyl-heptyl ester (32 mg, 0.058 mmol) in methanol (1 mL) was added potassium carbonate (100 mg, 0.724 mmol). The resulting solution was stirred for 2 hours then concentrated. The crude product was dissolved in a mixture of methylene chloride and water. The organic layer was dried over sodium sulfate, filtered and concentrated. Chromatography on silica gel gave the title compound (32 mg, >100%).

The title compounds for examples 2–15 were prepared by a method analogous to that described in Example 1.

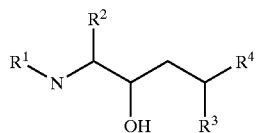

| EXAMPLE | R¹ | R² | R³ | R⁴ |
|---|---|---|---|---|
| 2 | | | | |

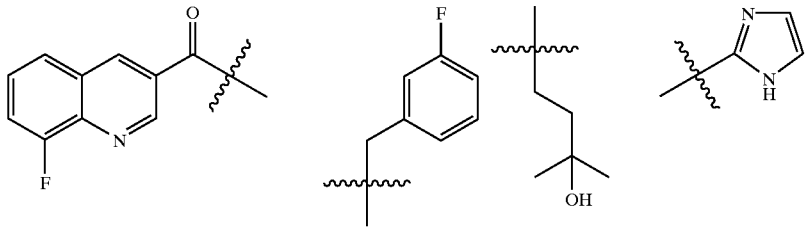

| 3 | | | | |

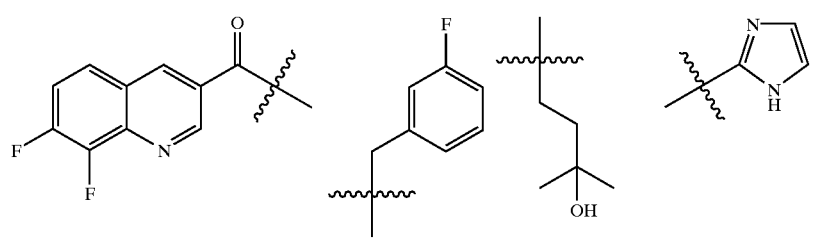

| 4 | | | | |

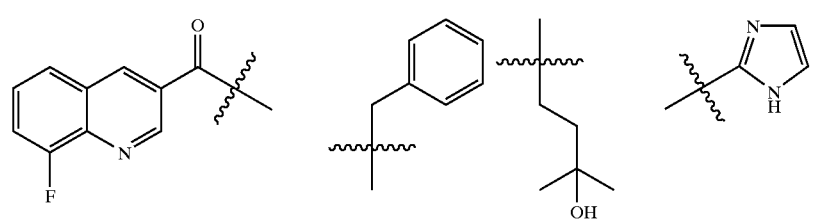

| 5 | | | | |

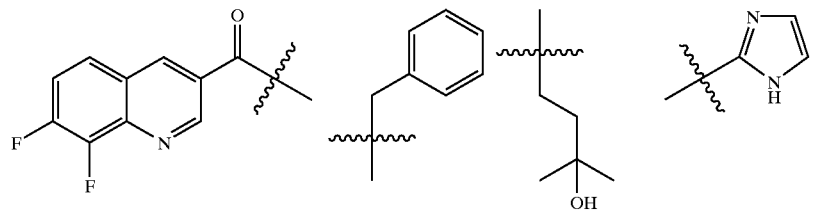

| 6 | | | | |

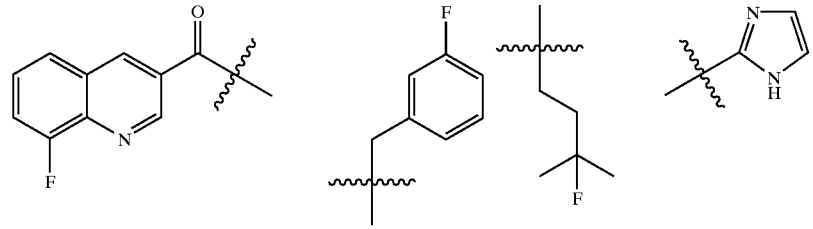

-continued
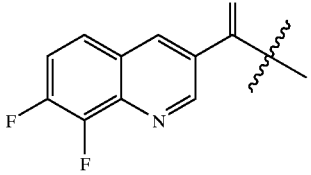
| EXAMPLE | R¹ | R² | R³ | R⁴ |
|---|---|---|---|---|
| 7 | 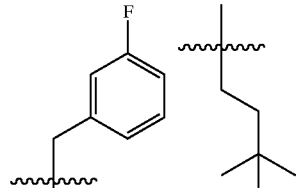 | 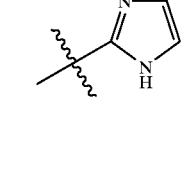 |  | 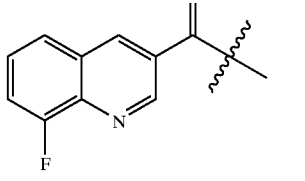 |
| 8 | 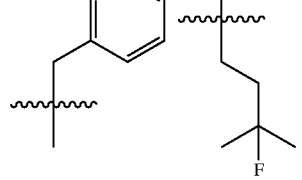 | 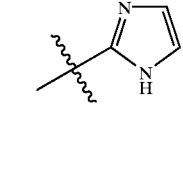 |  | 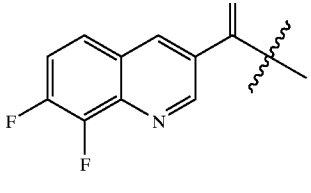 |
| 9 | 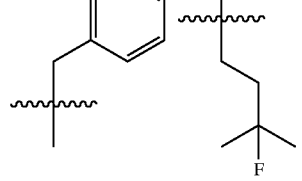 | 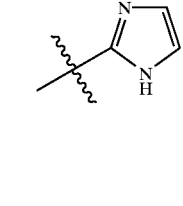 |  | 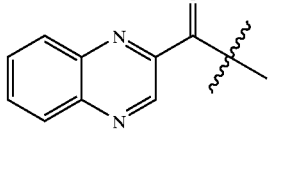 |
| 10 | 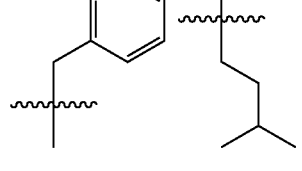 | 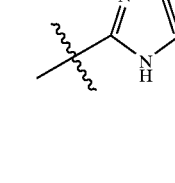 |  | 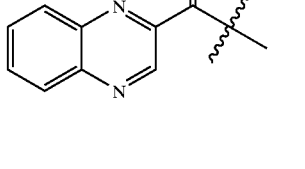 |
| 11 | 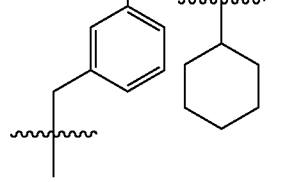 | 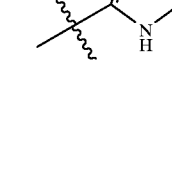 |  | 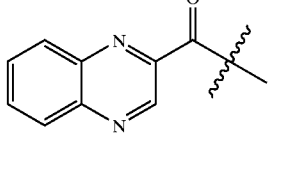 |
| 12 | 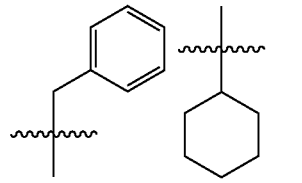 | 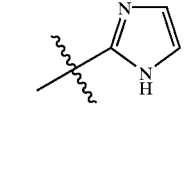 |  | |

-continued

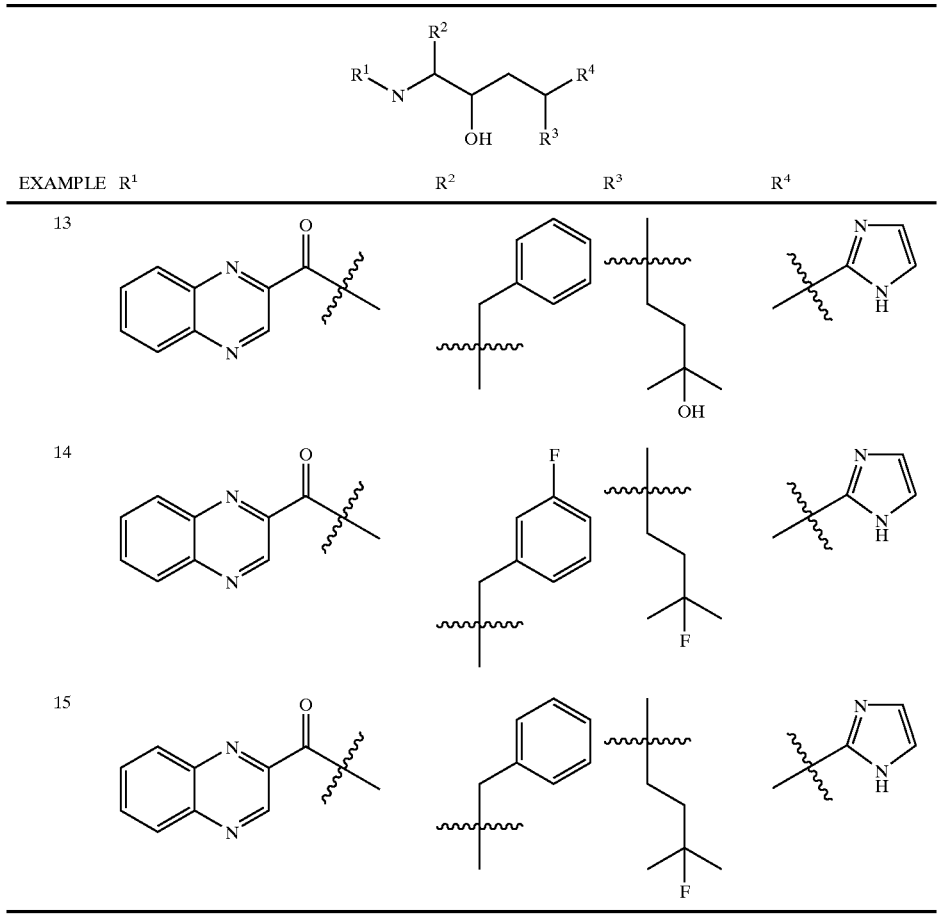

EXAMPLE 16
Quinoxaline-2-carboxylic acid [1-benzyl-7-fluoro-2-hydroxy-7-methyl-4-(4H-[1,2,4]triazol-3-yl)-octyl]-amide
Acetic acid 3-carbamoyl-6-fluoro-6-methyl-1-{2-phenyl-1-[(quinoxaline-2-carbonyl)-amino]-ethyl}-heptyl ester To a solution of quinoxaline-2-carboxylic acid (1-benzyl-4-carbamoyl-7-fluoro-2-hydroxy-7-methyl-octyl)-amide (1.01 g, 2.14 mmol) in pyridine (4 mL) was added dimethylaminopyridine (DMAP) (65 mg, 0.533 mmol) and acetic anhydride (0.400 mL, 4.23 mmol). The resulting solution was stirred for 2 hours, then diluted with methylene chloride and washed with 1 M hydrochloric acid. The organic layer was dried over sodium sulfate, filtered and concentrated to give the title compound as a white foam (1.16 g, >100%).

Acetic acid 3-(dimethylaminomethylene-carbamoyl)-6-fluoro-6-methyl-1-{2-phenyl-1-[(quinoxaline-2-carbonyl)-amino]-ethyl}-heptyl ester A solution of acetic acid 3-carbamoyl-6-fluoro-6-methyl-1-{2-phenyl-1-[(quinoxaline-2-carbonyl)-amino]-ethyl}-heptyl ester (522 mg, 1.03 mmol) in N,N-dimethylformamide dimethyl acetal (2 mL) was heated to 50° C. for two hours, cooled to ambient temperature and diluted with methylene chloride and water. The organic layer was washed with saturated aqueous sodium chloride, dried over sodium sulfate, filtered and concentrated to give the title compound as a white foam (580 mg, 100%).

Acetic acid 6-fluoro-6-methyl-1-{2-phenyl-1-[(quinoxaline-2-carbonyl)-amino]-ethyl}-3-(4H-[1,2,4]triazol-3-yl)-heptyl ester To a solution of acetic acid 3-(dimethylaminomethylene-carbamoyl)-6-fluoro-6-methyl-1-{2-phenyl-1-[(quinoxaline-2-carbonyl)-amino]-ethyl}-heptyl ester (580 mg, 1.03 mmol) in acetic acid (2.5 mL) was added hydrazine (35 wt. % in water, 0.040 mL). The resulting solution was heated to 50° C. for 4 hours, cooled to ambient temperature, diluted with ethyl acetate, and neutralized with saturated aqueous sodium bicarbonate. The organic later was dried over sodium sulfate, filtered, and concentrated to give the title compound as a white foam (580 mg, >100%).

Quinoxaline-2-carboxylic acid [1-benzyl-7-fluoro-2-hydroxy-7-methyl-4-(4H-[1,2,4]triazol-3-yl)-octyl]-amide To a solution of acetic acid 6-fluoro-6-methyl-1-{2-phenyl-1-[(quinoxaline-2-carbonyl)-amino]-ethyl}-3-(4H-[1,2,4]triazol-3-yl)-heptyl ester (575 mg, 1.08 mmol) in methanol (10 mL) was added potassium carbonate (276 mg, 2.00 mmol), stirred for 5 hours, and concentrated. The crude product was dissolved in ethyl acetate and water. The organic layer was then washed with saturated aqueous sodium chloride, dried over sodium sulfate, filtered and concentrated. Chromatography on silica gel gave the title compound (459 mg, 87%).

The title compounds for examples 17–18 were prepared by a method analogous to that described in Example 16.

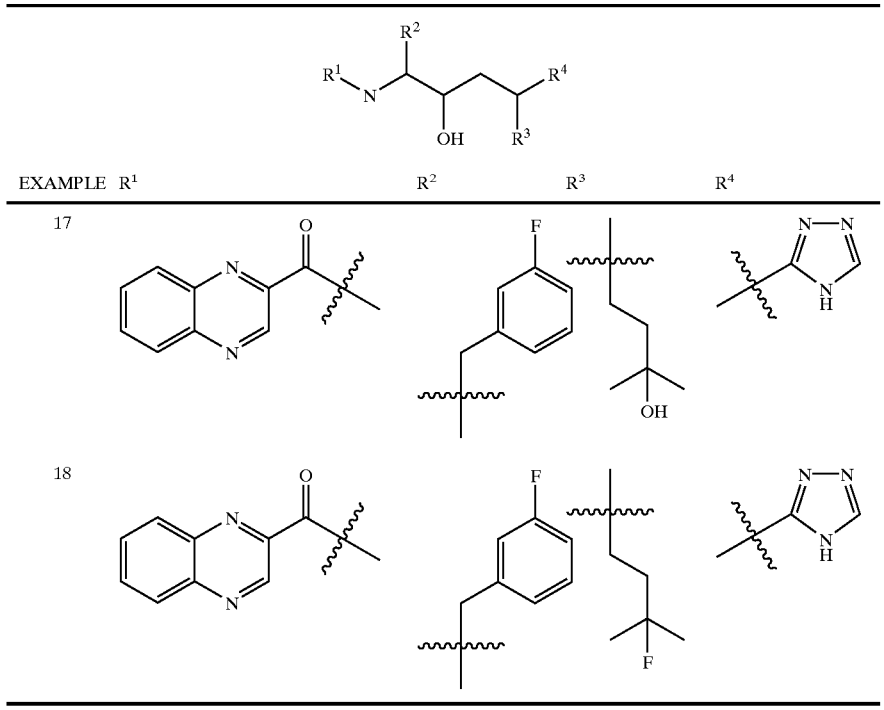

EXAMPLE 19

Quinoxaline-2-carboxylic acid [1-benzyl-4-(4,5-dihydro-1H-imidazol-2-yl)-7-fluoro-2-hydroxy-7-methyl-octyl]-amide Quinoxaline-2-carboxylic acid [1-benzyl-4-(4,5-dihydro-1H-imidazol-2-yl)-7-fluoro-2-hydroxy-7-methyl-octyl]-amide To a solution of ethylenediamine (0.040 mL, 0.598 mmol) in toluene (2 mL) at −10° C. was added trimethylaluminum (2.0 M in hexanes, 0.300 mL, 0.600 mmol) and stirred for 15 minutes. A solution of quinoxaline-2-carboxylic acid {1-[4-(3-fluoro-3-methyl-butyl)-5-oxo-tetrahydro-furan-2-yl]-2-phenyl-ethyl}-amide (250 mg, 0.556 mmol) in toluene (3 mL) was then added and the reaction warmed to ambient temperature, then heated to reflux for 3 hours. The reaction was cooled to ambient temperature and quenched carefully with water (1 mL). The solution was diluted with methylene chloride and methanol and then filtered, washing the filtrate with methanol. The organics were concentrated and the crude product was purified by chromatography on silica gel to give the title compound (74 mg, 17%).

The title compounds for examples 20–21 were prepared by a method analogous to that described in Example 19.

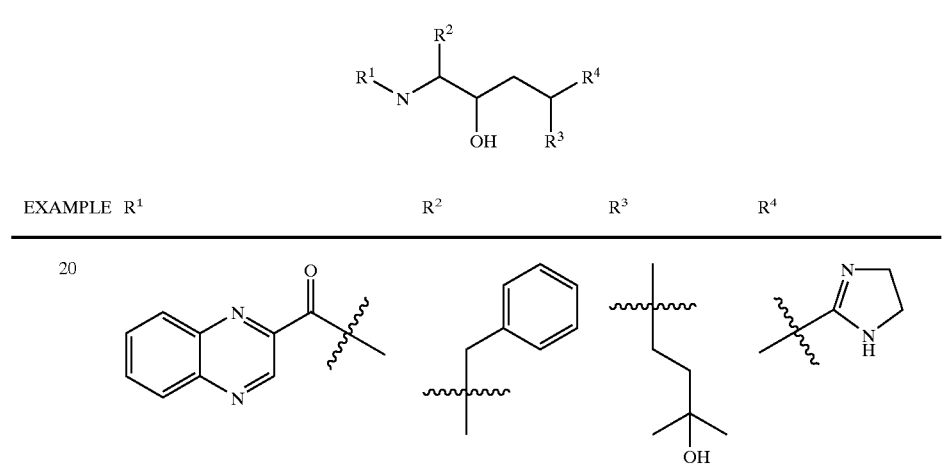

-continued

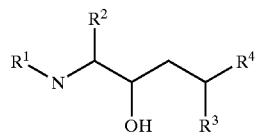

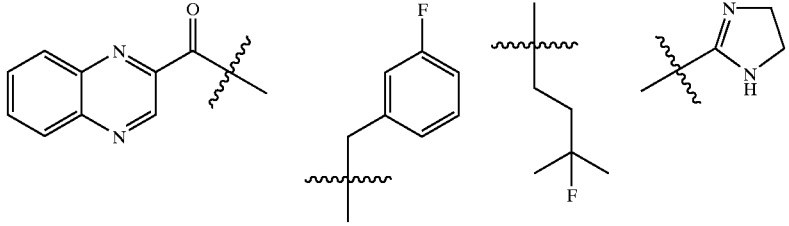

| EXAMPLE | R¹ | R² | R³ | R⁴ |
|---|---|---|---|---|

EXAMPLE 22

Quinoxaline-2-carboxylic acid [4-(5-amino-[1,3,4]oxadiazol-2-yl)-1-benzyl-7-fluoro-2-hydroxy-7-methyl-octyl]-amide Quinoxaline-2-carboxylic acid (1-benzyl-7-fluoro-4-hydrazinocarbonyl-2-hydroxy-7-methyl-octyl)-amide To a solution of quinoxaline-2-carboxylic acid {1-[4-(3-fluoro-3-methyl-butyl)-5-oxo-tetrahydro-furan-2-yl]-2-phenyl-ethyl}-amide (220 mg, 0.489 mmol) in methanol (5 mL) was added excess hydrazine (0.500 mL) and stirred for 18 hours. The reaction was concentrated to give the title compound (222 mg, 94%).

Quinoxaline-2-carboxylic acid [4-(5-amino-[1,3,4]oxadiazol-2-yl)-1-benzyl-7-fluoro-2-hydroxy-7-methyl-octyl]-amide To a solution of quinoxaline-2-carboxylic acid (1-benzyl-7-fluoro-4-hydrazinocarbonyl-2-hydroxy-7-methyl-octyl)-amide (110 mg, 0.228 mmol) in dioxane (0.5 mL) and water (0.5 mL) was added cyanogen bromide (31 mg, 0.296 mmol) and potassium hydrogencarbonate (31 mg, 0.310 mmol). The reaction was heated to reflux for 1 hour then cooled to ambient temperature. The dioxane/water was removed by adding benzene (5 mL) and concentrating (2×). The remaining solid was dissolved in ethyl acetate and water. The layers were separated and the aqueous layer extracted with ethyl acetate. The combined organics were dried over sodium sulfate and concentrated. Recrystallization of the crude product using a mixture of ethyl acetate, hexanes and methanol gave the title compound (64 mg, 55%).

The title compounds for examples 23–33 were prepared by a method analogous to that described in Example 22.

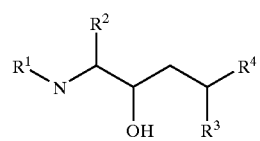

| EXAMPLE | R¹ | R² | R³ | R⁴ |
|---|---|---|---|---|

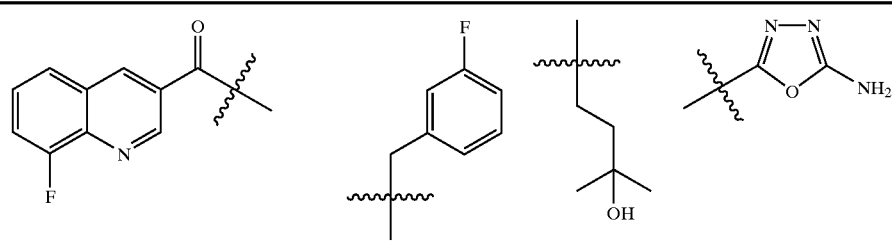

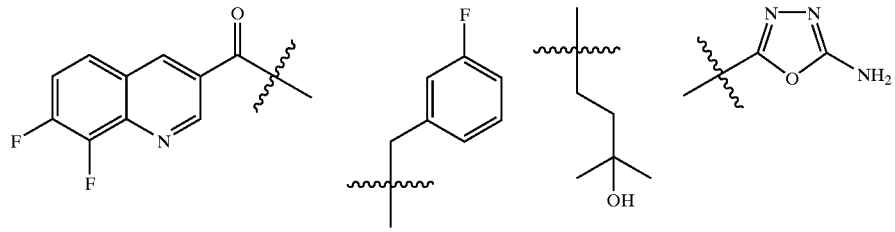

-continued
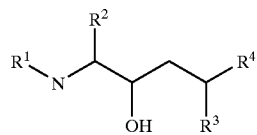
| EXAMPLE | R¹ | R² | R³ | R⁴ |
|---|---|---|---|---|
| 25 | 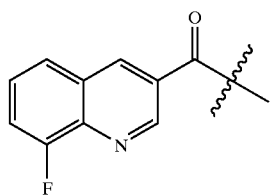 | 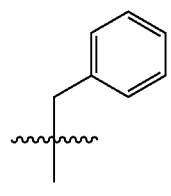 | 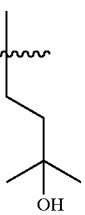 | 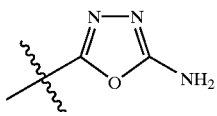 |
| 26 | 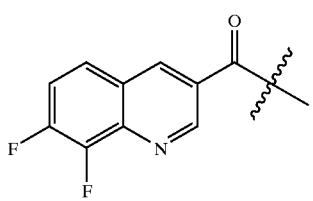 | 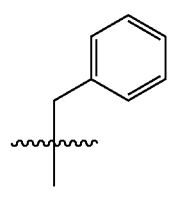 | 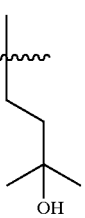 | 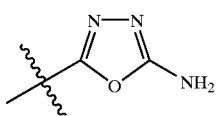 |
| 27 | 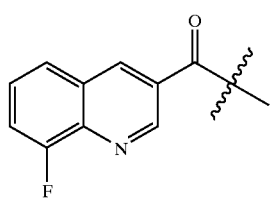 | 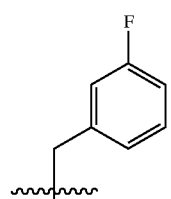 | 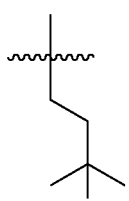 | 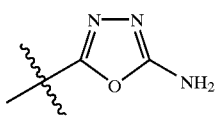 |
| 28 | 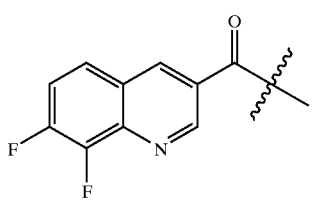 | 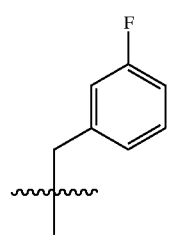 | 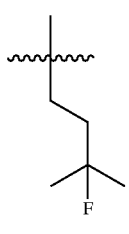 | 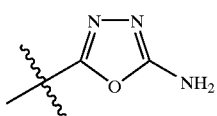 |

-continued

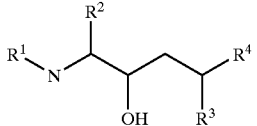

| EXAMPLE | R¹ | R² | R³ | R⁴ |
|---|---|---|---|---|
| 29 | 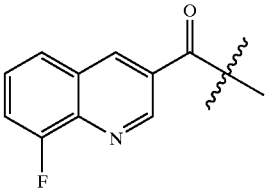 | 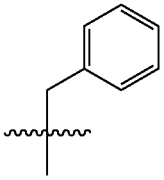 | 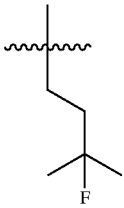 | 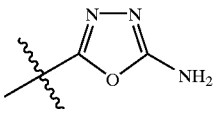 |
| 30 | 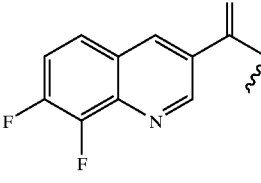 | 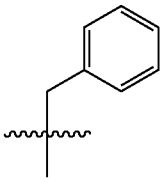 | 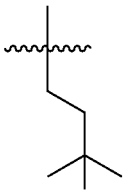 | 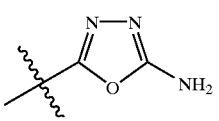 |
| 31 | 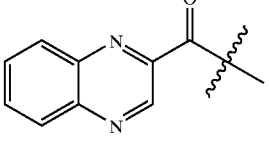 | 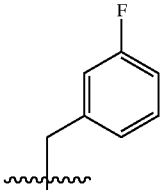 | 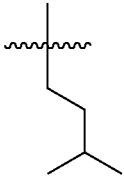 | 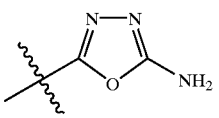 |
| 32 | 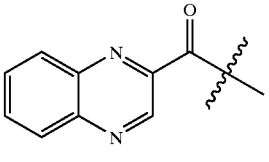 | 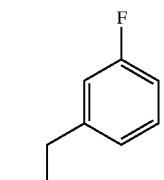 | 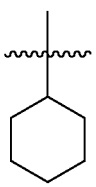 | 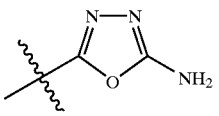 |
| 33 | 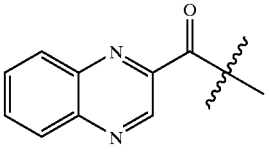 | 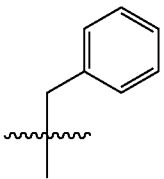 | 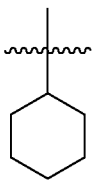 | 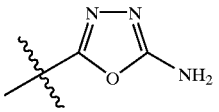 |

EXAMPLE 34

Quinoxaline-2-carboxylic acid [1-benzyl-7-fluoro-2-hydroxy-7-methyl-4-(5-oxo-4,5-dihydro-[1,3,4]oxadiazol-2-yl)-octyl]-amide Quinoxaline-2-carboxylic acid [1-benzyl-7-fluoro-2-hydroxy-7-methyl-4-(5-oxo-4,5-dihydro-[1,3,4]oxadiazol-2-yl)-octyl]-amide To a solution of quinoxaline-2-carboxylic acid (1-benzyl-7-fluoro-4-hydrazinocarbonyl-2-hydroxy-7-methyl-octyl)-amide (62 mg, 0.129 mmol) in tetrahydrofuran (2 mL) was added triethylamine (0.018, 0.129 mmol) at 0° C. was added carbonyldiimidazole (23 mg, 0.142 mmol). The reaction was allowed to warm to ambient temperature and stirred a total of 20 hours before diluting with ethyl acetate (10 mL) and hexane (2 mL). The mixture was washed with saturated aqueous ammonium chloride, saturated aqueous sodium bicarbonate, and saturated aqueous sodium chloride. The organic layer was dried over magnesium sulfate, filtered and concentrated. Chromatography on silica gel gave the title compound (54 mg, 82%).

The title compounds for examples 35–36 were prepared by a method analogous to that described in Example 34.

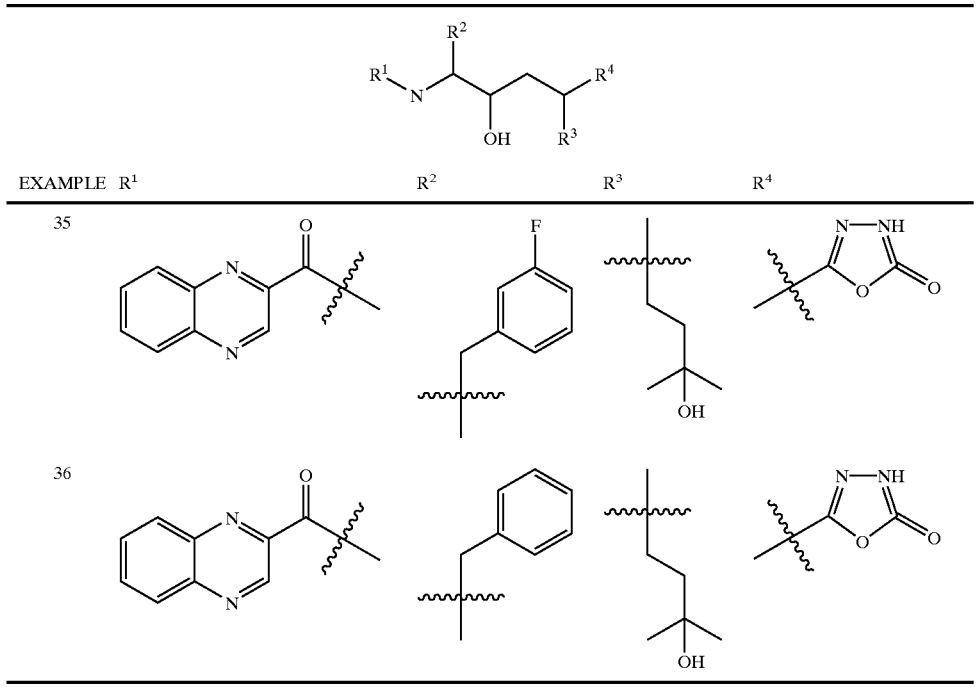

EXAMPLE 37

Quinoxaline-2-carboxylic acid [1-benzyl-4-(4,5-dihydro-oxazol-2-yl)-7-fluoro-2-hydroxy-7-methyl-octyl]-amide 2-(3-Fluoro-3-methy-butyl)-4-hydroxy-6-phenyl-5-[(quinoxaline-2-carbonyl)-amino]-hexanoic acid To a solution of quinoxaline-2-carboxylic acid {1-[4-(3-fluoro-3-methyl-butyl)-5-oxo-tetrahydro-furan-2-yl]-2-phenyl-ethyl}-amide (4 g, 8.90 mmol) in tetrahydrofuran was added lithium hydroxide (1 M in water, 28 mL) and stirred for 2 hours. The reaction was then concentrated, and concentrated from benzene (2×) to give the title compound (4.2 g, 100%).

4-(tert-Butyl-dimethyl-silanyloxy)-2-(3-fluoro-3-methyl-butyl)-6-phenyl-5-[(quinoxaline-2-carbonyl)-amino]-hexanoic acid To a solution of 2-(3-fluoro-3-methyl-butyl)-4-hydroxy-6-phenyl-5-[(quinoxaline-2-carbonyl)-amino]-hexanoic acid (1.63 g, 3.49 mmol) in dimethylformamide (10 mL) was added t-butyldimethylsilyl choride (3.2 g, 20.9 mmol) and imidazole (2.9 g, 41.9 mmol). The reaction was stirred for 4 days then quenched with methanol and stirred another 0.5 hours. The solution was diluted with ether and water. The organic layer was washed with saturated aqueous sodium chloride, dried over magnesium sulfate, filtered and concentrated. Chromatography on silica gel gave the title compound (784 mg, 39%).

Quinoxaline-2-carboxylic acid [1-benzyl-2-(tert-butyl-dimethyl-silanyloxy)-7-fluoro-4-(2-hydroxy-ethylcarbamoyl)-7-methyl-octyl]-amide To a solution of 4-(tert-butyl-dimethyl-silanyloxy)-2-(3-fluoro-3-methyl-butyl)-6-phenyl-5-[(quinoxaline-2-carbonyl)-amino]-hexanoic acid (515 mg, 0.885 mmol) in methylene chloride (9 mL) was added ethanolamine (0.080 mL, 1.33 mmol), 1-hydroxybenzotriazole (215 mg, 1.59 mmol), 1-(3-dimethylaminopropyl)-3-ethylcarbodiimide hydrochloride (288 mg, 1.50 mmol) and triethylamine (0.247 mL, 1.77 mmol). The resulting solution was stirred for 17 hours then diluted with ethyl acetate and washed with water then saturated aqueous sodium chloride. The organic layer was then dried over sodium sulfate, filtered, and concentrated. Chromatography on silica gel gave the title compound (343 mg, 62%).

Quinoxaline-2-carboxylic acid [1-benzyl-2-(tert-butyl-dimethyl-silanyloxy)-4-(4 5-dihydro-oxazol-2-yl)-7-fluoro-7-methyl-octyl]-amide To a solution of quinoxaline-2-carboxylic acid [1-benzyl-2-(tert-butyl-dimethyl-silanytoxy)-7-fluoro-4-(2-hydroxy-ethylcarbamoyl)-7-methyl-octyl]-amide (100 mg, 0.160 mmol) in methylene chloride (1.5 mL) was added triphenylphosphine (63 mg, 0.240 mmol), hexachloroethane (57 mg, 0.240 mmol), and triethylamine (0.045 mL, 0.320 mmol). The on was stirred for 2 hours than chromatographed directly on silica gel to give the title compound (72.5 mg, 75%).

Quinoxaline-2-carboxylic acid [1-benzyl-4-(4,5-dihydro-oxazol-2-yl )-7-fluoro-2-hydroxy-7-methyl-octyl]-amide To a solution of quinoxaline-2-carboxylic acid [1-benzyl-2-(tert-butyl-dimethyl-silanyloxy)-4-(4,5-dihydro-oxazol-2-yl)-7-fluoro-7-methyl-octyl]-amide (41 mg, 0.068 mmol) in tetrahydrofuran (0.70 mL) was added tris(dimethylamino) sulfur (trimethylsilyl)difluoride (56 mg, 0.203 mmol). The reaction was stirred for 1 hour then quenched with methanol and concentrated. Chromatography on silica gel gave the title compound (27.8 mg, 84%).

The title compounds for examples 38–49 were prepared by a method analogous to described in Example 37.

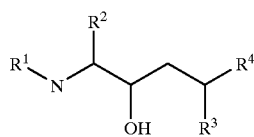
| EXAMPLE | R¹ | R² | R³ | R⁴ |
|---|---|---|---|---|
| 38 | 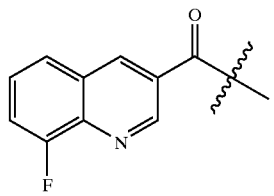 | 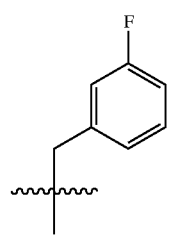 | 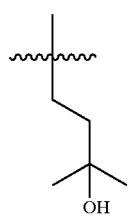 | 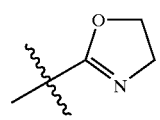 |
| 39 | 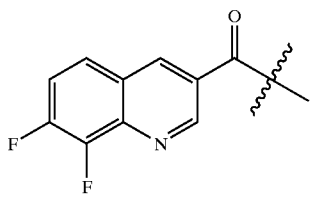 | 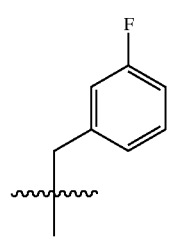 | 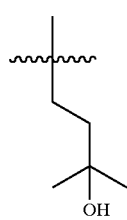 | 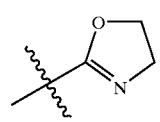 |
| 40 | 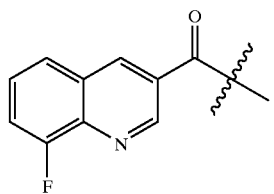 | 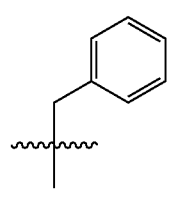 | 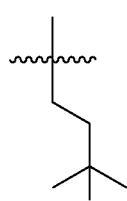 | 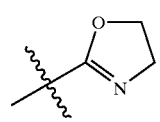 |
| 41 | 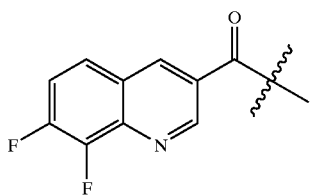 | 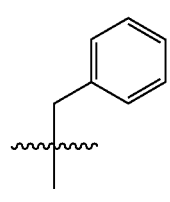 | 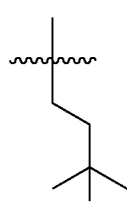 | 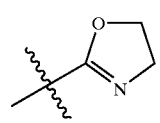 |
| 42 | 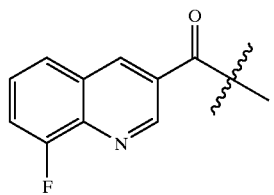 | 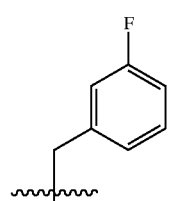 | 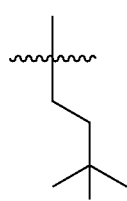 | 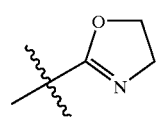 |
| 43 | 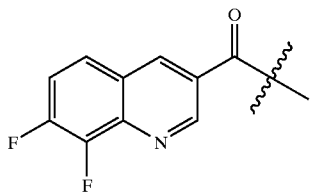 | 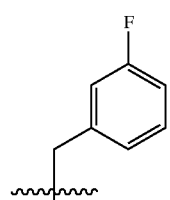 | 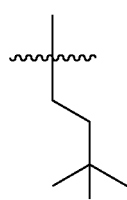 | 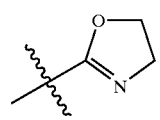 |

-continued

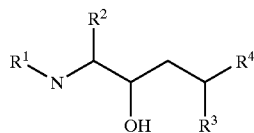

| EXAMPLE | R¹ | R² | R³ | R⁴ |
|---|---|---|---|---|
| 44 | 8-fluoroquinoline-3-carbonyl (C(CH₃)) | benzyl | CH₂C(CH₃)₂F (neopentyl-F) | 4,5-dihydrooxazol-2-yl (C(CH₃)) |
| 45 | 7,8-difluoroquinoline-3-carbonyl (C(CH₃)) | benzyl | CH₂C(CH₃)₂F | 4,5-dihydrooxazol-2-yl (C(CH₃)) |
| 46 | quinoxaline-2-carbonyl (C(CH₃)) | 3-fluorobenzyl | isobutyl (CH₂CH(CH₃)₂) | 4,5-dihydrooxazol-2-yl (C(CH₃)) |
| 47 | quinoxaline-2-carbonyl (C(CH₃)) | benzyl | cyclohexyl | 4,5-dihydrooxazol-2-yl (C(CH₃)) |
| 48 | quinoxaline-2-carbonyl (C(CH₃)) | 3-fluorobenzyl | cyclohexyl | 4,5-dihydrooxazol-2-yl (C(CH₃)) |
| 49 | quinoxaline-2-carbonyl (C(CH₃)) | benzyl | cyclohexylmethyl | 4,5-dihydrooxazol-2-yl (C(CH₃)) |

EXAMPLE 50

Quinoxaline-2-carboxylic acid (1-benzyl-7-fluoro-2-hydroxy-7-methyl-4-oxazol-2-yl-octyl)-amide Quinoxaline-2-carboxylic acid [1-benzyl-2-(tert-butyl-dimethyl-silanyloxy)-7-fluoro-7-methyl-4-(2-oxo-ethylcarbamoyl)-octyl]-amide To a solution of quinoxaline-2-carboxylic acid [1-benzyl-2-(tert-butyl-dimethyl-silanyloxy)-7-fluoro-4-(2-hydroxy-ethylcarbamoyl)-7-methyl-octyl]-amide (250 mg, 0.400 mmol) in methylene chloride was added 1,1,1-triacetoxy-1,1-dihydro-1,2-benziodoxol-3(1H)-one [Dess-Martin periodinane] (340 mg, 0.800 mmol). The reaction was stirred for 2 hours and then diluted with ether and quenched with a 1:1 mixture of saturated aqueous sodium thiosulfate-:sodium bicarbonate. The layers were separated and the aqueous layer extracted with ethyl acetate. The combined organics were washed with a 1:1 mixture of saturated aqueous sodium thiosulfate:sodium bicarbonate, water, and saturated sodium chloride. The organic layer was then dried over sodium sulfate, filtered, and concentrated. Chromatography on silica gel gave the title compound (233 mg, 94%).
Quinoxaline-2-carboxylic acid [1-benzyl-2-(tert-butyl-dimethyl-silanyloxy)-7-fluoro-7-methyl-4-oxazol-2-yl-octyl]-amide To a solution of quinoxaline-2-carboxylic acid [1-benzyl-2-(tert-butyl-dimethyl-silanyloxy)-7-fluoro-7-methyl-4-(2-oxo-ethylcarbamoyl)-octyl]-amide (230 mg, 0.369 mmol) in methylene chloride (3.5 mL) was added triphenylphosphine (145 mg, 0.554 mmol), hexachloroethane (131 mg, 0.554 mmol) and triethylamine (0.103 mL, 0.739 mmol). The reaction was stirred for 16 hours than concentrated. Chromatography on silica gel gave the title compound (137 mg, 62%).
Quinoxaline-2-carboxylic acid (1-benzyl-7-fluoro-2-hydroxy-7-methyl-4-oxazol-2-yl-octyl)-amide To a solution of quinoxaline-2-carboxylic acid [1-benzyl-2-(tert-butyl-dimethyl-silanyloxy)-7-fluoro-7-methyl-4-oxazol-2-yl-octyl]-amide (133 mg, 0.220 mmol) in tetrahydrofuran (2 mL) was added tris(dimethylamino)sulfur (trimethylsilyl)difluoride (180 mg, 0.660 mmol). The reaction was stirred for 1 hour then quenched with methanol and concentrated. Chromatography on silica gel gave the title compound (73 mg, 68%).

The title compounds for examples 51–61 were prepared by a method analogous to that described in Example 50.

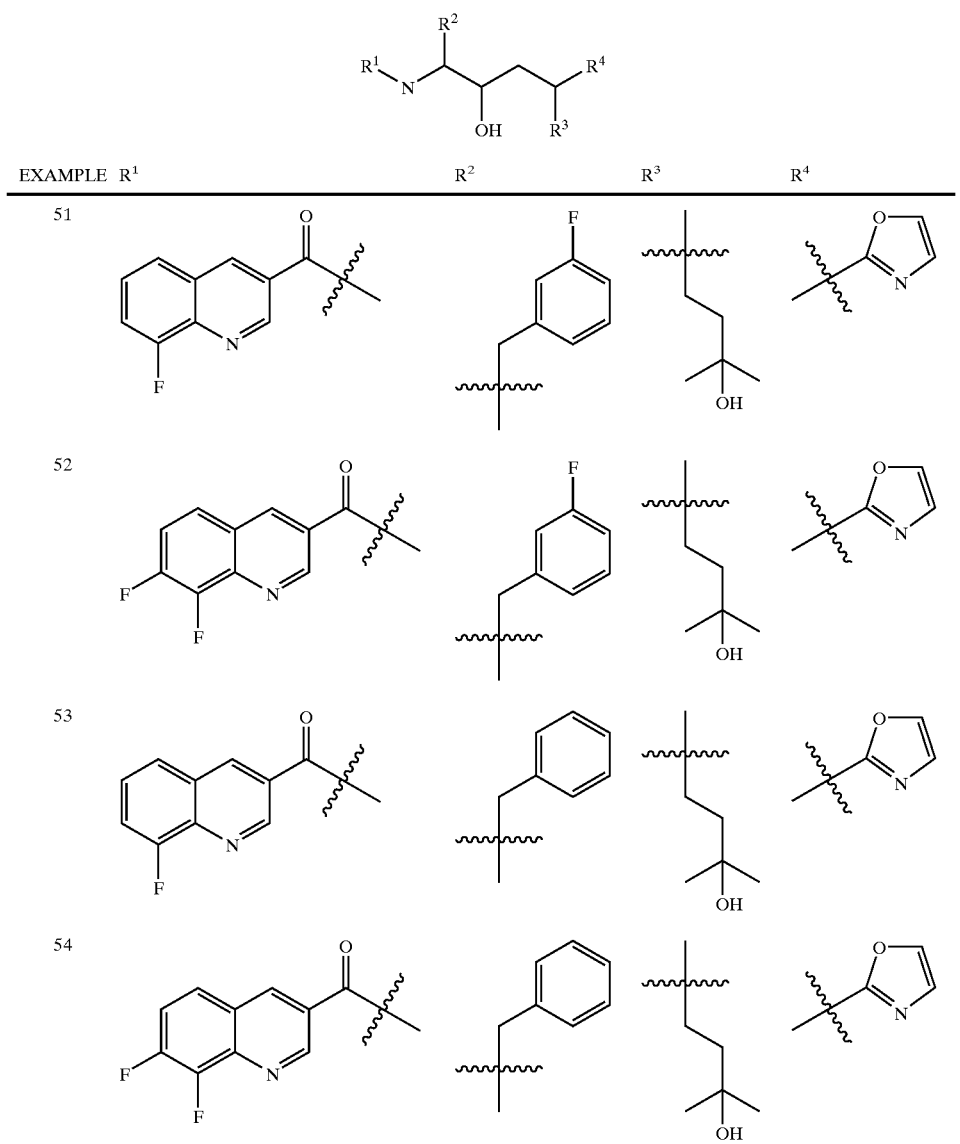

-continued

| EXAMPLE | R¹ | R² | R³ | R⁴ |
|---------|----|----|----|----|
| 55 | 8-fluoroquinolin-3-yl-C(O)-C(CH₃)₂- | 3-fluorobenzyl | 2-fluoro-2-methylpropyl | oxazol-2-yl-C(CH₃)₂- |
| 56 | 7,8-difluoroquinolin-3-yl-C(O)-C(CH₃)₂- | 3-fluorobenzyl | 2-fluoro-2-methylpropyl | oxazol-2-yl-C(CH₃)₂- |
| 57 | 8-fluoroquinolin-3-yl-C(O)-C(CH₃)₂- | benzyl | 2-fluoro-2-methylpropyl | oxazol-2-yl-C(CH₃)₂- |
| 58 | 7,8-difluoroquinolin-3-yl-C(O)-C(CH₃)₂- | benzyl | 2-fluoro-2-methylpropyl | oxazol-2-yl-C(CH₃)₂- |
| 59 | quinoxalin-2-yl-C(O)-C(CH₃)₂- | 3-fluorobenzyl | isobutyl | oxazol-2-yl-C(CH₃)₂- |
| 60 | quinoxalin-2-yl-C(O)-C(CH₃)₂- | 3-fluorobenzyl | cyclohexyl | oxazol-2-yl-C(CH₃)₂- |

-continued

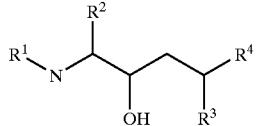

| EXAMPLE | R¹ | R² | R³ | R⁴ |
|---|---|---|---|---|
| 61 | 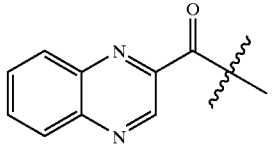 | 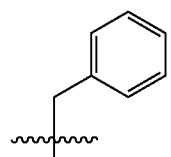 | 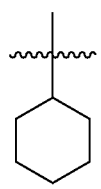 | 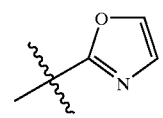 |

EXAMPLE 62

Quinoxaline-2-carboxylic acid (4-benzenesulfonyl-1-benzyl-2-hydroxy-7-methyl-octyl)-amide
(4-Benzenesulfonyl-1-benzyl-2-hydroxy-7-methyl-octvl)-carbamic acid benzyl ester To a solution of 3.0 equivalents of (4-methyl-pentane-1-sulfonyl)-benzene (previously prepared by Gaoni, *J. Org. Chem.* 1982, 47, 2564) in tetrahydrofuran cooled to –78° C. is added 3.0 equivalents of n-butyl lithium and stirred for 30 min. One equivalent of (1-oxiranyl-2-phenyl-ethyl)-carbamic acid benzyl ester (previously prepared by Kaldor, et al. *J. Med. Chem.*, 1997, p. 3979) in THF is then added dropwise and the reaction stirred for 1.5 h. The reaction is then quenched with saturated aqueous sodium bicarbonate and warmed to ambient temperature. After standard aqueous work-up and extraction, followed by concentration and silica gel chromatography the title compound is obtained.
2-Amino-5-benzenesulfonyl-8-methyl-1-phenyl-nonan-3-ol To a solution of (4-benzenesulfonyl-1-benzyl-2-hydroxy-7-methyl-octyl)-carbamic acid benzyl ester in ethanol is added 10 mole % palladium hydroxide on carbon. The mixture is then shaken on a Parr shaker under 50 psi of hydrogen for approximately 18 h. The catalyst is filtered off and the solution concentrated to give the title compound.
Quinoxaline-2-carboxylic acid (4-benzenesulfonyl-1-benzyl-2-hydroxy-7-methyl-octyl)-amide To a solution of one equivalent of 2-amino-5-benzenesulfonyl-8-methyl-1-phenyl-nonan-3-ol in methylene chloride is added 1.05 equivalents each of 2-quinoxalinecarboxylic acid, N-methyl morpholine, and O-benzotriazol-1-yl-N,N,N',N'-teteramethyluronium hexafluorophosphate. The reaction mixture is stirred at ambient temperature for 18 h. After standard aqueous work-up and extraction, followed by concentration and silica gel chromatography the title compound is obtained.

The title compounds for examples 63–72 are prepared by a method analogous to that described in Example 62.

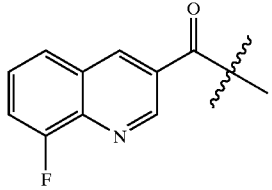

| EXAMPLE | R¹ | R² | R³ | R⁴ |
|---|---|---|---|---|
| 63 | 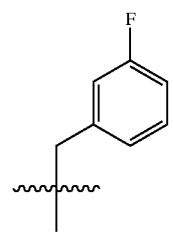 | 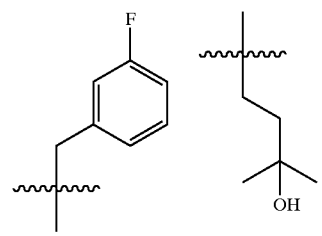 | 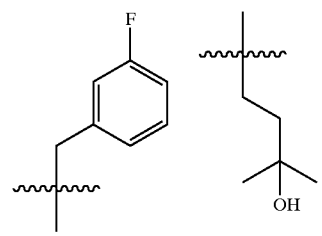 | 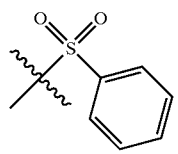 |

-continued
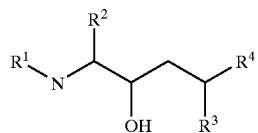
| EXAMPLE | R¹ | R² | R³ | R⁴ |
|---|---|---|---|---|
| 64 | 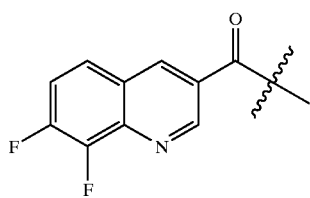 | 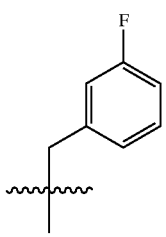 | 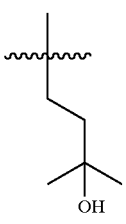 | 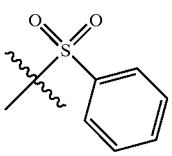 |
| 65 | 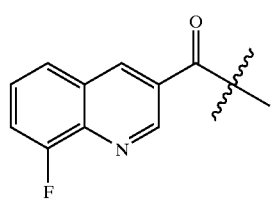 | 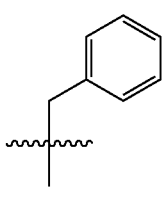 | 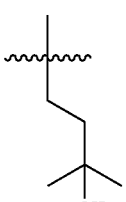 | 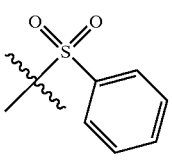 |
| 66 | 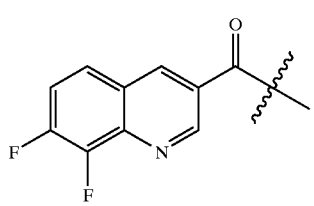 | 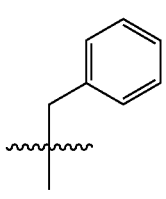 | 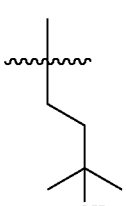 | 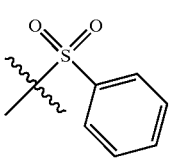 |
| 67 | 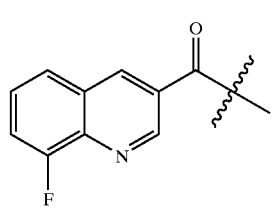 | 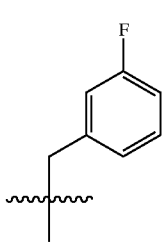 | 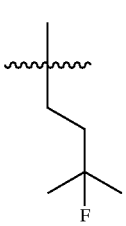 | 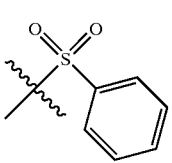 |
| 68 | 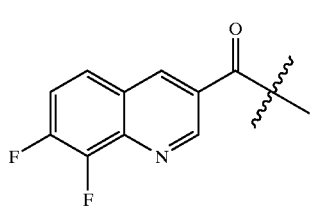 | 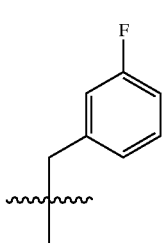 | 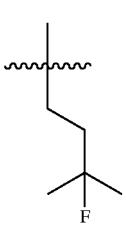 | 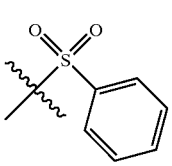 |

-continued

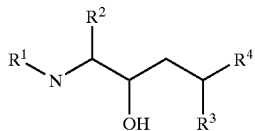

| EXAMPLE | R¹ | R² | R³ | R⁴ |
|---|---|---|---|---|
| 69 | 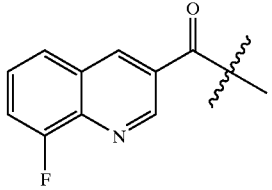 | 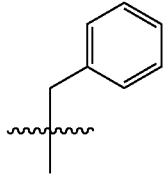 | 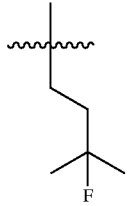 | 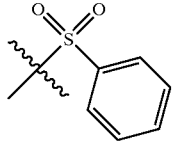 |
| 70 | 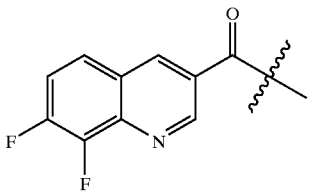 | 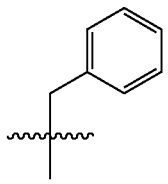 | 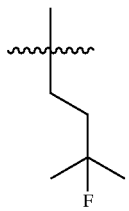 | 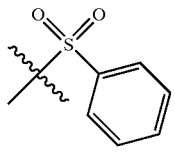 |
| 71 | 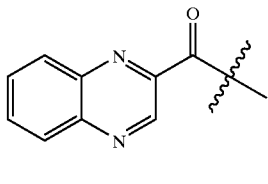 | 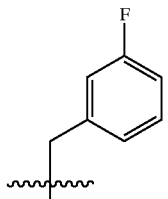 | 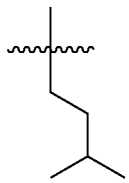 | 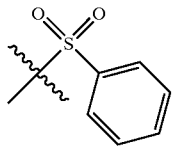 |
| 72 | 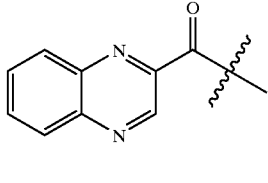 | 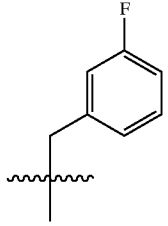 | 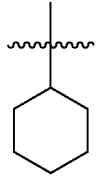 | 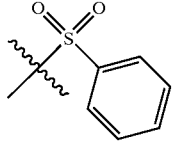 |

EXAMPLE 73

Quinoxaline-2-carboxylic acid (1-benzyl-7-fluoro-2-hydroxy-7-methyl-4-thiocarbamoyl-octyl)-amide Acetic acid 6-fluoro-6-methyl-1-2-phenyl-1-[(quinoxaline-2-carbonyl)-amino]-ethyl-3-thiocarbamoyl-heptyl ester To a solution of 1.0 equivalent of acetic acid 3-carbamoyl-6-fluoro-6-methyl-1-{2-phenyl-1-[(quinoxaline-2-carbonyl)-amino]-ethyl}-heptyl ester in tetrahydrofuran cooled to 0° C. is added 0.5 equivalents of Lawesson's reagent dropwise. The yellow suspension is allowed to warm to room temperature and stirred for about 5 h. The reaction mixture is concentrated to dryness, then purified by silica gel chromatography to give the title compound.

Quinoxaline-2-carboxylic acid (1-benzyl-7-fluoro-2-hydroxy-7-methyl-4-thiocarbamoyl-octyl)-amide To a solution of 1.0 equivalents of acetic acid 6-fluoro-6-methyl-1-{2-phenyl-1-[(quinoxaline-2-carbonyl)-amino]-ethyl}-3-thiocarbamoyl-heptyl ester in methanol is added 2.0 equivalents of potassium carbonate, stirred for approximately 5 hours, and concentrated. The crude product is dissolved in ethyl acetate and water. The organic layer is then washed with saturated aqueous sodium chloride, dried over sodium sulfate, filtered and concentrated. Chromatography on silica gel gives the title compound.

The title compounds for examples 74–76 are prepared by a method analogous to that described in Example 73.

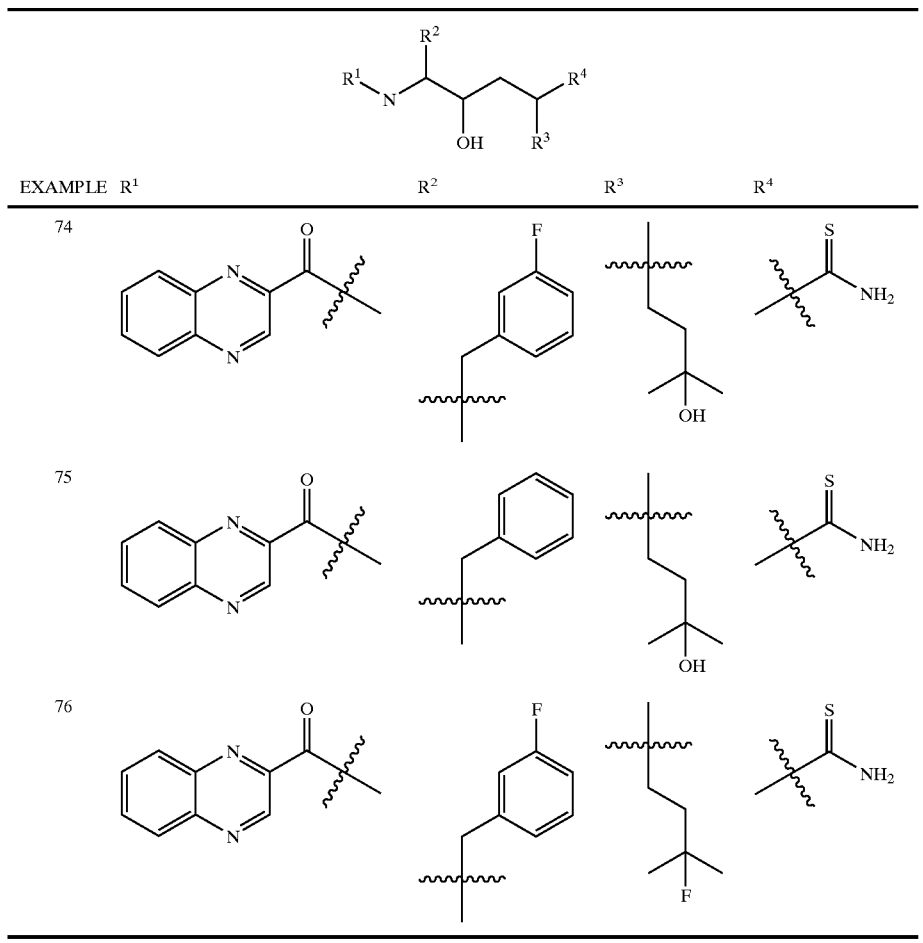

EXAMPLE 77
Quinoxaline-2-carboxylic acid (1-benzyl-4-carbamimidoyl-7-fluoro-2-hydroxy-7-methyl-octyl)-amide
Acetic acid 3-carbamimidoyl-6-fluoro-6-methyl-1-{2-phenyl-1-[(quinoxaline-2-carbonyl)-amino]-ethyl}-heptyl ester To a solution of acetic acid 6-fluoro-6-methyl-1-{2-phenyl-1-[(quinoxaline-2-carbonyl)-amino]-ethyl}-3-thiocarbamoyl-heptyl ester in acetone is added excess methyl iodide. The reaction is then refluxed for approximately 2 h, then cooled and concentrated. The crude product is taken up in saturated solution of ammonia in methanol and stirred for approximately 15 hrs. The reaction mixture is concentrated to dryness, then purified by silica gel chromatography to give the title compound.

Quinoxaline-2-carboxylic acid (1-benzyl-4-carbamimidoyl-7-fluoro-2-hydroxy-7-methyl-octyl)-amide To a solution of 1.0 equivalents of acetic acid 3-carbamimidoyl-6-fluoro-6-methyl-1-{2-phenyl-1-[(quinoxaline-2-carbonyl)-amino]-ethyl}-heptyl ester in methanol is added 2.0 equivalents of potassium carbonate, stirred for approximately 5 hours, and concentrated. The crude product is dissolved in ethyl acetate and water. The organic layer is then washed with saturated aqueous sodium chloride, dried over sodium sulfate, filtered and concentrated. Chromatography on silica gel gives the title compound.

The title compounds for examples 78–80 are prepared by a method analogous to that described in Example 77.

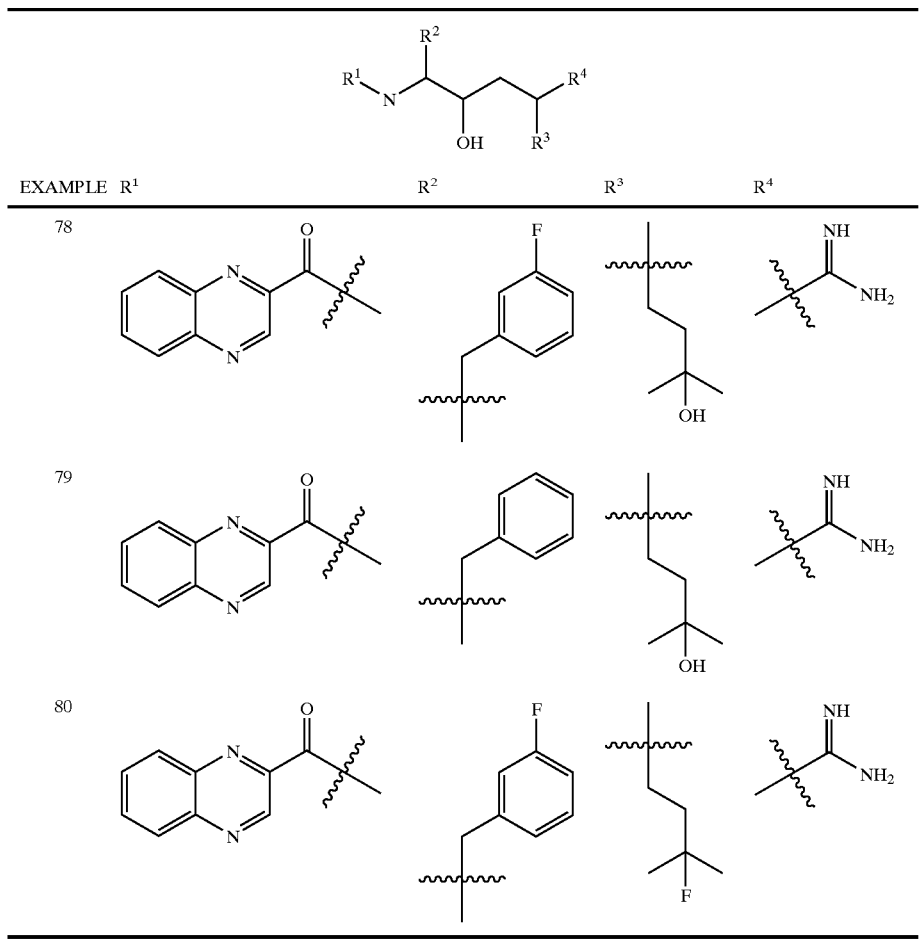

EXAMPLE 81
Quinoxaline-2-carboxylic acid [4-(acetylimino-aminomethyl)-1-benzyl-7-fluoro-2-hydroxy-7-methyl-octyl]-amide
Quinoxaline-2-carboxylic acid [4-(acetylimino-aminomethyl)-1-benzyl-7-fluoro-2-hydroxy-7-methyl-octyl]-amide To a solution of 1.0 equivalents of quinoxaline-2-carboxylic acid (1-benzyl-4-carbamimidoyl-7-fluoro-2-hydroxy-7-methyl-octyl)-amide in methylene chloride is added 1.0 equivalents of triethylamine followed by 1.0 equivalents of acetyl chloride. The reaction is stirred at ambient temperature for approximately 5 hours. After standard aqueous work-up and extraction, followed by concentration and silica gel chromatography the title compound is obtained.

The title compounds for examples 82–86 are prepared by a method analogous to that described in Example 81.

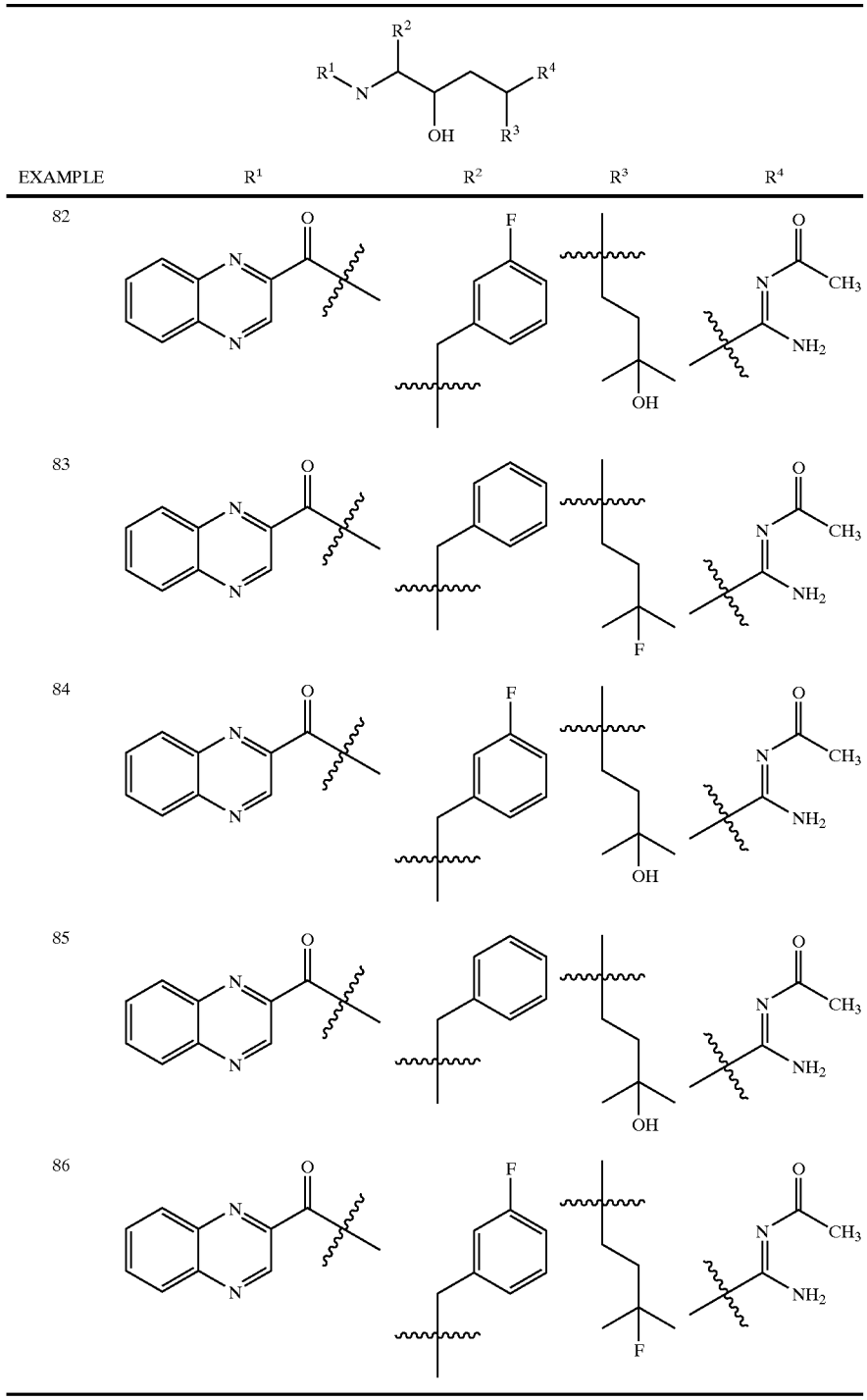

EXAMPLE 87

Quinoxaline-2-carboxylic acid [4-(amino-methanesulfonylimino-methyl)-1-benzyl-1-fluoro-2-hydroxy-7-methyl-octyl]-amide Quinoxaline-2-carboxylic acid [4-(amino-methanesulfonylimino-methyl)-1-benzyl-7-fluoro-2-hydroxy-7-methyl-octyl]-amide To a solution of 1.0 equivalents of quinoxaline-2-carboxylic acid (1-benzyl-4-carbamimidoyl-7-fluoro-2-hydroxy-7-methyl-octyl)-amide in methylene chloride is added 1.0 equivalents of triethylamine followed by 1.0 equivalents of methanesulfonyl chloride. The reaction is stirred at ambient temperature for approximately 5 hours. After standard aqueous work-up and extraction, followed by concentration and silica gel chromatography the title compound is obtained.

The title compounds for examples 88–94 are prepared by a method analogous to that described in Example 87.

| EXAMPLE | R¹ | R² | R³ | R⁴ |
|---|---|---|---|---|
| 88 | 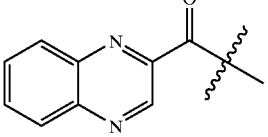 | 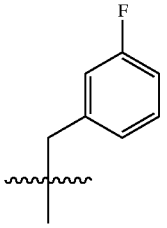 | 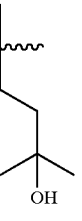 | 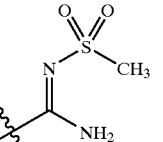 |
| 89 | 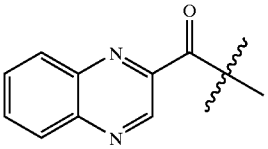 | 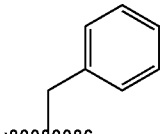 | 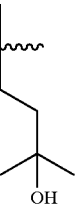 | 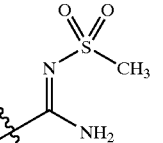 |
| 90 | 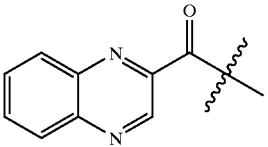 | 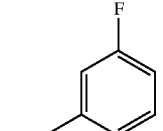 | 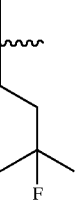 | 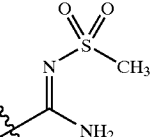 |
| 91 | 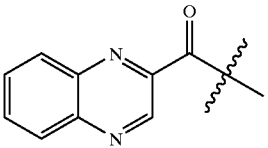 | 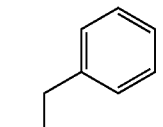 | 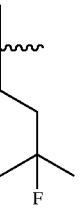 | 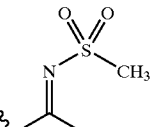 |
| 92 | 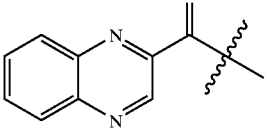 | 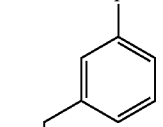 | 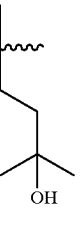 | 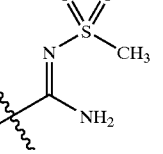 |
| 93 | 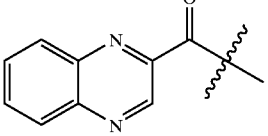 | 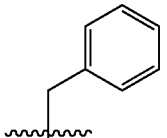 | 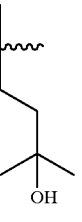 | 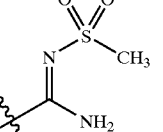 |

-continued

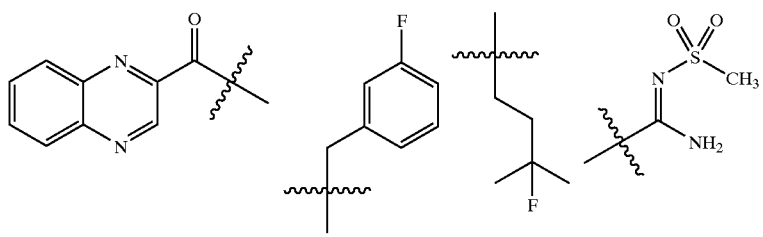

| EXAMPLE | R¹ | R² | R³ | R⁴ |
| --- | --- | --- | --- | --- |
| 94 | 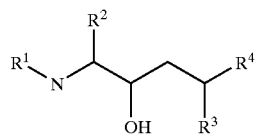 | | | |

EXAMPLE 95

Quinoxaline-2-carboxylic acid [4-(cyanoimino-amino-methyl)-1-benzyl-7-fluoro-2-hydroxy-7-methyl-octyl]-amide Quinoxaline-2-carboxylic acid [4-(cyanoimino-amino-methyl)-1-benzyl-7-fluoro-2-hydroxy-7-methyl-octyl]-amide To a solution of 1.0 equivalents of quinoxaline-2-carboxylic acid (1-benzyl-4-carbamimidoyl-7-fluoro-2-hydroxy-7-methyl-octyl)-amide in methylene chloride is added 1.0 equivalents of cyanogen bromide. The reaction is stirred at ambient temperature for approximately 15 hours. After standard aqueous work-up and extraction, followed by concentration and silica gel chromatography the title compound is obtained.

The title compounds for examples 96–98 are prepared by a method analogous to that described in Example 95.

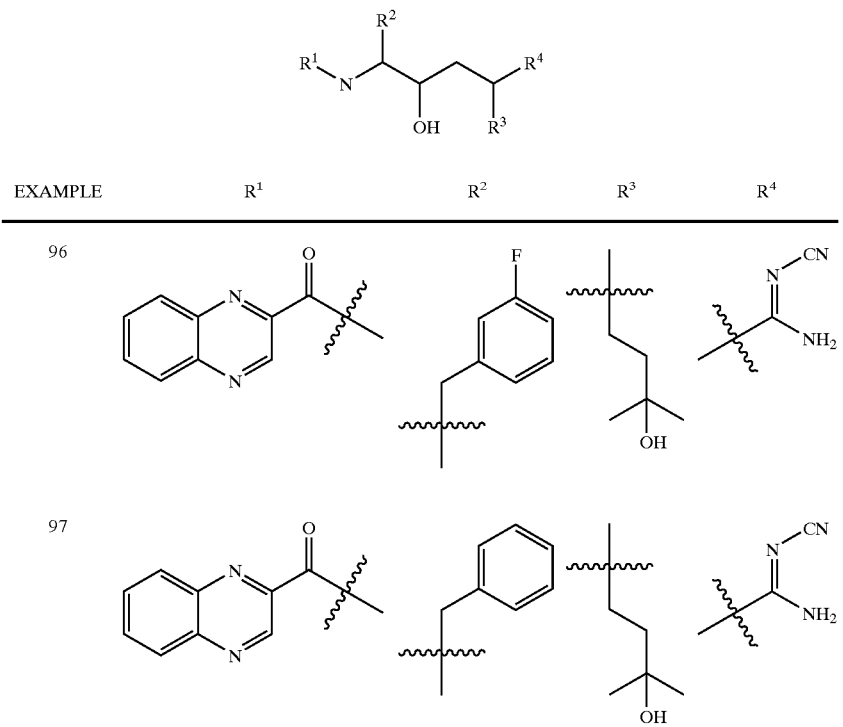

-continued

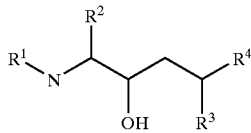

| EXAMPLE | R¹ | R² | R³ | R⁴ |
|---|---|---|---|---|
| 98 |  |  |  |  |

What is claimed is:

1. A compound of the formula

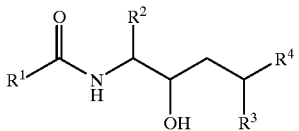   I or the pharmaceutically acceptable salt thereof; wherein $R^1$ is quinoxalinyl optionally substituted with one or more substituents independently selected from the group consisting of hydrogen, deuterium, halo, CN, ($C_1$–$C_6$) alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$) alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$) alkyl-(C=O)—O—, ($C_1$–$C_6$)alkyl-(C=O)—O—($C_1$–$C_6$)alkyl, H(O=C)—, H(O=C)—($C_1$–$C_6$)alkyl, ($C_1$–$C_6$)alkyl(O=C)—, ($C_1$–$C_6$)alkyl(O=C)—($C_1$–$C_6$)alkyl, NO₂, amino, ($C_1$–$C_6$)alkylamino, [($C_1$–$C_6$)alkyl]₂amino, amino($C_1$–$C_6$)alkyl, ($C_1$–$C_6$) alkylamino($C_1$–$C_6$)alkyl, [($C_1$–$C_6$)alkyl]₂amino ($C_1$–$C_6$)alkyl, H₂N—(C=O)—, ($C_1$–$C_6$)alkyl-NH—(C=O)—, [($C_1$–$C_6$)alkyl]₂N—(C=O)—, H₂N (C=O)—($C_1$–$C_6$)alkyl, ($C_1$–$C_6$)alkyl-HN(C=O)—($C_1$–$C_6$)alkyl, [($C_1$–$C_6$)alkyl]₂N—(C=O)—($C_1$–$C_6$) alkyl, H(O=C)—NH—, $C_1$–$C_6$)alkyl(C=O)—NH, ($C_1$–$C_6$)alkyl(C=O)—[NH]($C_1$–$C_6$)alkyl, ($C_1$–$C_6$) alkyl(C=O)—[N($C_1$–$C_6$)alkyl], ($C_1$–$C_6$)alkyl, ($C_1$–$C_6$)alkyl-S—, ($C_1$–$C_6$)alkyl-(S=O)—, ($C_1$–$C_6$) alkyl-SO₂—, ($C_1$–$C_6$)alkyl-SO₂—NH—, H₂N—SO₂—, H₂N—SO₂—($C_1$–$C_6$)alkyl, ($C_1$–$C_6$) alkylHN—SO₂—($C_1$–$C_6$)alkyl, [($C_1$–$C_6$)alkyl]₂N—SO₂—($C_1$–$C_6$)alkyl, CF₃SO₃—, ($C_1$–$C_6$)alkyl-SO₃—, phenyl, ($C_3$–$C_{10}$)cycloalkyl, ($C_2$–$C_9$)heterocycloalkyl, and ($C_2$–$C_9$)heteroaryl;

$R^2$ is phenyl-(CH₂)$_m$—, naphthyl-(CH₂)$_m$—, ($C_3$–$C_{10}$) cycloalkyl-(CH₂)$_m$—, ($C_1$–$C_6$)alkyl or ($C_2$–$C_9$) heteroaryl-(CH₂)$_m$—, wherein m is an interger from zero to four; wherein each of said phenyl, naphthyl, ($C_3$–$C_{10}$)cycloalkyl or ($C_2$–$C_9$)heteroaryl moieties of said phenyl-(CH₂)$_m$—, naphthyl-(CH₂)$_m$—, ($C_3$–$C_{10}$) cycloalkyl-(CH₂)$_m$— or ($C_2$–$C_9$)heteroaryl-(CH₂)$_m$— groups may optionally be substituted with one or more substituents independently selected from hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$) alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$) alkyl-O—(C=O)—($C_1$–$C_6$)alkyl, ($C_1$–$C_6$)alkyl-(C=O)—O—, ($C_1$–$C_6$)alkyl-(C=O)—O—($C_1$–$C_6$) alkyl, H(O=C)—, H(O=C)—($C_1$–$C_6$)alkyl, ($C_1$–$C_6$) alkyl(O=C)—, ($C_1$–$C_6$)alkyl(O=C)—($C_1$–$C_6$)alkyl, NO₂, amino, ($C_1$–$C_6$)alkylamino, [($C_1$–$C_6$)alkyl]₂amino, amino($C_1$–$C_6$)alkyl, ($C_1$–$C_6$)alkylamino ($C_1$–$C_6$)alkyl, [($C_1$–$C_6$)alkyl]₂amino($C_1$–$C_6$)alkyl, H₂N—(C=O)—, ($C_1$–$C_6$)alkyl-NH—(C=O)—, [($C_1$–$C_6$)alkyl]₂N—(C=O)—, H₂N(C=O)—($C_1$–$C_6$) alkyl, ($C_1$–$C_6$) alkyl-HN(C=O )—($C_1$–$C_6$)alkyl, [($C_1$–$C_6$)alkyl]₂N—(C=O)—($C_1$–$C_6$)alkyl, H(O=C)—NH—, ($C_1$–$C_6$)alkyl(C=C)—NH, ($C_1$–$C_6$)alkyl(C=C)—[NH]($C_1$–$C_6$)alkyl, ($C_1$–$C_6$) alkyl(C=O)—[N($C_1$–$C_6$)alkyl]($C_1$–$C_6$)alkyl, ($C_1$–$C_6$) alkyl-S—, ($C_1$–$C_6$)alkyl-(S=O)—, ($C_1$–$C_6$)alkyl-SO₂—, ($C_1$–$C_6$)alkyl-SO₂—NH—, H₂N—SO₂—, H₂N—SO₂($C_1$–$C_6$)alkyl, ($C_1$–$C_6$)alkylHN—SO₂—($C_1$–$C_6$)alkyl, [($C_1$–$C_6$)alkyl]₂N—SO₂—($C_1$–$C_6$)alkyl, CF₃SO₃—, ($C_1$–$C_{6)alkyl-SO3}$—, phenyl, phenoxy, benzyloxy, ($C_3$–$C_{10}$)cycloalkyl, ($C_2$–$C_9$) heterocycloalkyl, and ($C_2$–$C_9$)heteroaryl;

$R^3$ is hydrogen, deuterium, ($C_1$–$C_{10}$)alkyl, ($C_3$–$C_{10}$) cycloalkyl-(CH₂)$_n$—, ($C_2$–$C_9$)heterocycloalkyl-(CH₂)$_n$—, ($C_2$–$C_9$)heteroayl-(CH₂)$_n$— or aryl-(CH₂)$_n$—; wherin n is an interger from zero to six;

wherein said $R^3$ ($C_1$–$C_{10}$)alkyl group may optionally be substituted with one or more substituents, independently selected from hydrogen, deuterium, halo, CN, ($C_1$–$C_6$)alkyl optionally substituted with one or more fluorine atoms, hydroxy, hydroxy-($C_1$–$C_6$)alkyl, ($C_1$–$C_6$)alkoxy optionally substituted with one or more fluorine atoms, ($C_1$–$C_6$)alkoxy($C_1$–$C_6$)alkyl, HO—(C=O)—, ($C_1$–$C_6$)alkyl-O—(C=O)—, HO—(C=O)—($C_1$–$C_6$)alkyl, ($C_1$–$C_6$)alkyl-O—(C=O)—($C_1$–$C_6$)alkyl, ($C_1$–$C_6$)alkyl-(C=O)—O—, ($C_1$–$C_6$) alkyl-(C=O)—O—($C_1$–$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino ($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2$N—(C=O)—, ($C_1$-$C_6$)alkyl-NH—(C=O)—, [($C_1$-$C_6$)alkyl]$_2$N—(C=O)—, $H_2$N(C=O)—($C_1$-$C_6$)alkyl, ($C_1$-$C_6$)alkyl-HN(C=O)—($C_1$-$C_6$)alkyl, [($C_1$-$C_6$)alkyl]N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—, $H_2$N—$SO_2$—, $H_2$N—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; and wherein any of the carbon—carbon single bonds of said ($C_1$-$C_{10}$)alkyl may optionally be replaced by a carbon—carbon double bond;

wherein the ($C_3$-$C_{10}$)cycloalkyl moiety of said $R^3$ ($C_3$-$C_{10}$)cycloalkyl-$(CH_2)_n$—group may optionally be substituted by one to three substitutents independently selected from the group consisting of hydrogen, deuterium, halo, CN, ($C_1$-$C_6$)alkyl optionally substituted with one or more fluorine atoms, hydroxy, hydroxy-($C_1$-$C_6$)alkyl, ($C_1$-$C_6$)alkoxy optionally substituted with one or more fluorine atoms, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$c_6$)alkyl, H(O=C)—H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino ($C_1$-$C_6$)alkylamino [($C_1$-$C_6$)alkyl]$_2$amino, amino ($C_1$-$C_6$)alkyl, ($C_1$-$C_6$)alkylamino ($C_1$-$C_6$)alkyl, [($C_1$-$C_6$)alkyl]$_2$amino($C_1$-$C_6$)alkyl, $H_2$N—(C=O)—, ($C_1$-$C_6$)alkyl-NH—(C=O)—, [($C_1$-$C_6$)alkyl]$_2$N—(C=O), $H_2$N(C=O)—($C_1$-$C_6$) alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl (S=O)—, (S=O)—, ($C_1$-$C_6$)alkyl-$SO_2$—, ($C_1$-$C_6$)alkyl-$SO_2$—NH—, $H_2$N—$SO_2$—, $H_2$N—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl,and ($C_2$-$C_9$)heteroaryl;

wherein the ($C_2$-$C_9$)heterocycloalkyl moiety of said $R^3$ ($C_2$-$C_9$)heterocycloalkyl-$(CH_2)_n$— group has from one to three heteroatoms independently selected from nitrogen, sulfur, oxygen, >S(=O), >$SO_2$ or >$NR^6$, wherein said ($C_2$-$C_9$)heterocycloalkyl moiety of said ($C_2$-$C_9$)heterocycloalkyl-$(CH_2)_n$— group may optionally be substituted on any of the ring carbon atoms capable of forming an additional bond with a substituent independently selected from the group consisting of hydrogen, deuterium, halo, CN, ($C_1$-$C_6$)alkyl optionally substituted with one or more fluorine atoms, hydroxy, hydroxy-($C_1$-$C_6$)alkyl, ($C_1$-$C_6$)alkoxy optionally substituted with one or more fluorine atoms, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino ($C_1$-$C_6$)alkyl, $H_2$N—(C=O)—, ($C_1$-$C_6$)alkyl-NH—(C=O)—, [($C_1$-$C_6$)alkyl]$_2$N—(C=O)—, $H_2$N (C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2$N—$SO_2$—, $H_2$N—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl;

wherein the ($C_2$-$C_9$)heteroaryl moiety of said $R^3$ ($C_2$-$C_9$)heteroaryl-$(CH_2)_n$— group has from one to three heteroatoms independently selected from nitrogen, sulfur or oxygen wherein said ($C_2$-$C_9$)heteroaryl moiety of said ($C_2$-$C_9$)heteroaryl-$(CH_2)_n$— group may optionally be substituted on any of the ring carbon atoms capable of forming an additional bond with a substituent selected from the group consisting of hydrogen, deuterium, halo, CN, ($C_1$-$C_6$)alkyl optionally substituted with one or more fluorine atoms, hydroxy, hydroxy-($C_1$-$C_6$)alkyl, ($C_1$-$C_6$)alkoxy optionally substituted with one or more fluorine atoms, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl-(C=O)—O—, ($C_1$-$C_6$)alkyl-(C=O)—O—($C_1$-$C_6$)alkyl, H(O=C)—, H(O=C)—($C_1$-$C_6$)alkyl, ($C_1$-$C_6$)alkyl(O=C)—, ($C_1$-$C_6$)alkyl(O=C)—($C_1$-$C_6$)alkyl, $NO_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, $H_2$N—(C=O)—, ($C_1$-$C_6$)alkyl-NH—(C=O)—, [($C_1$-$C_6$)alkyl]$_2$N—(C=O)—, $H_2$N(C=O)—($C_1$-$C_6$)alkyl, ($C_1$-$C_6$)alkyl-HN(C=O)—($C_1$-$C_6$)alkyl, [($C_1$-$C_6$)alkyl]$_2$N—(C=O)—($C_1$-$C_6$)alkyl, H(O=C)—NH—, ($C_1$-$C_6$)alkyl(C=O)—NH, ($C_1$-$C_6$)alkyl(C=O)—[NH]($C_1$-$C_6$)alkyl, ($C_1$-$C_6$)alkyl(C=O)—[N($C_1$-$C_6$)alkyl]($C_1$-$C_6$)alkyl, ($C_1$-$C_6$)alkyl-S—, ($C_1$-$C_6$)alkyl-(S=O)—, ($C_1$-$C_6$)alkyl-$SO_2$—, ($C_1$-$C_6$)alkyl-$SO_2$—NH—, $H_2$N—$SO_2$—, $H_2$N—$SO_2$—($C_1$-$C_6$)alkyl, ($C_1$-$C_6$)alkylHN—$SO_2$—($C_1$-$C_6$)alkyl, [($C_1$-$C_6$)alkyl]$_2$N—$SO_2$—($C_1$-$C_6$)alkyl, $CF_3SO_3$—, ($C_1$-$C_6$)alkyl-$SO_3$—, phenyl, ($C_3$-$C_{10}$)cycloalkyl, ($C_2$-$C_9$)heterocycloalkyl, and ($C_2$-$C_9$)heteroaryl; and wherein said aryl moiety of said $R^3$ aryl-$(CH_2)_n$— group is optionally substituted phenyl or naphthyl, wherein said phenyl and naphthyl may optionally be substituted with from one to three substituents independently selected from the group consisting of hydrogen, deuterium, halo, CN, ($C_1$-$C_6$)alkyl optionally substituted with one or more fluorine atoms, hydroxy, hydroxy-($C_1$-$C_6$)alkyl, ($C_1$-$C_6$)alkoxy optionally substituted with one or more fluorine atoms, ($C_1$-$C_6$)alkoxy($C_1$-$C_6$)alkyl, HO—(C=O)—, ($C_1$-$C_6$)alkyl-O—(C=O)—, HO—(C=O)—($C_1$-$C_6$)alkyl, ($C_1$-$C_6$)alkyl-O—(C=O)—($C_1$-$C_6$)alkyl, ($C_1$-$C_6$)alkyl- (C=O)—O—, $(C_1-C_6)$alkyl-(C=O)—O—$(C_1-C_6)$ alkyl, H(O=C)—, H(O=C)—$(C_1-C_6)$alkyl, $(C_1-C_6)$ alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino $(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$ alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$ alkyl(C=O)—[N$(C_1-C_6)$alkyl]$(C_1-C_6)$alkyl-S—, $(C_1-C_6)$alkyl, $(C_1-C_6)$alkyl-S—, $(C_1-C_6)$ alkyl-(S=O)—$(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$ alkyl-$SO_3$—, phenyl, $(C_3-C_{10})$cycloalkyl, $(C_2-C_9)$heterocycloalkyl, and $(C_2-C_9)$heteroaryl; and $R^4$ is $(C_2-C_9)$heteroaryl, $(C_2-C_9)$heterocycloalkyl, $R^5R^6N$-sulfonyl or a group of the formula

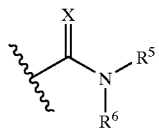

wherein $R^5$ is hydrogen, deuterium, $(C_1-C_6)$alkyl, hydroxy, $(C_1-C_6)$alkoxy, hydroxy$(C_1-C_6)$alkyl, $(C_1-C_6)$alkoxy(C=O)—, $(C_3-C_{10})$cycloalkyl-$(CH_2)_p$—, $(C_2-C_9)$heterocycloalkyl-$(CH_2)_p$—, $(C_2-C_9)$ heteroaryl-$(CH_2)_p$—, phenyl-$(CH_2)_p$—, or naphthyl-$(CH_2)_p$—, wherein p is an integer from zero to four; wherein said $(C_2-C_9)$heterocycloalkyl, $(C_2-C_9)$ heteroaryl, phenyl and naphthyl groups of said $(C_2-C_9)$ heterocycloalkyl-$(CH_2)_p$—, $(C_2-C_9)$heteroaryl-$(CH_2)_p$—, phenyl-$(CH_2)_p$—, or naphthyl-$(CH_2)_p$— may be optionally substituted on any of the ring atoms capable of supporting an additional bond with a substituent selected from the group consisting of hydrogen, halo, CN, $(C_1-C_6)$alkyl optionally substituted with one or more fluorine atoms, hydroxy, hydroxy-$(C_1-C_6)$alkyl, $(C_1-C_6)$alkoxy, optionally substituted with one or more fluorine atoms, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$ alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino $(C_1-C_6)$alkyl, $(C_1-C_6)$alkylamino$(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$ alkyl (C=O)—NH, $(C_1-C_6)$alkyl(C=O)—[NH] $(C_1-C_6)$alkyl, $(C_1-C_6)$alkyl(C=O)—[N$(C_1-C_6)$alkyl] $(C_1-C_6)$alkyl, $(C_1-C_6)$alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$cycloalkyl, $(C_2-C_9)$heterocycloalkyl, and $(C_2-C_9)$heteroaryl;

or $R^5$ and $R^6$ together with the nitrogen atom to which they are attached form a $(C_2-C_9)$heterocycloalkyl group wherein any of the ring atoms of said $(C_2-C_9)$ heterocycloalkyl group may optionally be substituted with a substituent selected from the group consisting of hydrogen, halo, CN, $(C_1-C_6)$alkyl optionally substituted with one or more fluorine atoms, hydroxy, hydroxy-$(C_1-C_6)$alkyl, $(C_1-C_6)$alkoxy optionally substituted with one or more fluorine atoms, $(C_1-C_6)$ alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$ alkyl-O—(C=O)—$(C_1-C_6)$alkyl, $(C_1-C_6)$alkyl-(C=O)—O—, $(C_1-C_6)$alkyl-(C=O)—O—$(C_1-C_6)$ alkyl, H(O=C)—, H(O=C)—$(C_1-C_6)$alkyl, $(C_1-C_6)$ alkyl(O=C)—, $(C_1-C_6)$alkyl(O=C)—$(C_1-C_6)$alkyl, $NO_2$, amino, $(C_1-C_6)$alkylamino, $[(C_1-C_6)$alkyl$]_2$amino, amino$(C_1-C_6)$alkyl, $(C_1-C_6)$alkylamino $(C_1-C_6)$alkyl, $[(C_1-C_6)$alkyl$]_2$amino$(C_1-C_6)$alkyl, $H_2N$—(C=O)—, $(C_1-C_6)$alkyl-NH—(C=O)—, $[(C_1-C_6)$alkyl$]_2N$—(C=O)—, $H_2N(C=O)$—$(C_1-C_6)$ alkyl, $(C_1-C_6)$alkyl-HN(C=O)—$(C_1-C_6)$alkyl, $[(C_1-C_6)$alkyl$]_2N$—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$ alkyl(C=O)—[N$(C_1-C_6)$alkyl]$(C_1-C_6)$alkyl, $(C_1-C_6)$ alkyl-S—, $(C_1-C_6)$alkyl-(S=O)—, $(C_1-C_6)$alkyl-$SO_2$—, $(C_1-C_6)$alkyl-$SO_2$—NH—, $H_2N$—$SO_2$—, $H_2N$—$SO_2$—$(C_1-C_6)$alkyl, $(C_1-C_6)$alkylHN—$SO_2$—$(C_1-C_6)$alkyl, $[(C_1-C_6)$alkyl$]_2N$—$SO_2$—$(C_1-C_6)$alkyl, $CF_3SO_3$—, $(C_1-C_6)$alkyl-$SO_3$—, phenyl, $(C_3-C_{10})$ cycloalkyl, $(C_2-C_9)$heterocycloalkyl, and $(C_2-C_9)$ heteroaryl;

$R^6$ is hydrogen, deuterium, $(C_1-C_6)$alkyl or amino;

X is $NR^7$ or S wherein $R^7$ is defined as $R^4$ above; and with the proviso that when $R^4$ is a five-membered heterocyclic group, either $R^2$ or $R^3$ must be substituted by a functional group other than $(C_1-C_6)$alkyl, hydroxy$(C_1-C_6)$ alkyl, $(C_1-C_6)$alkoxy, $(C_1-C_6)$alkyl-(C=O)—O—, $(C_1-C_6)$ alkyl-(C=O)—O—$(C_1-C_6)$alkyl, amino, $(C_1-C_6)$ alkylamino, $[(C_1-C_6)$alkyl$]_2$amino, amino$(C_1-C_6)$alkyl, benzofuryl, indolyl, azacycloalkyl, azabicycloalkyl or benzopiperidinyl.

2. A compound according to claim 1, wherein said compound of formula I has the exact stereochemistry depicted in formula

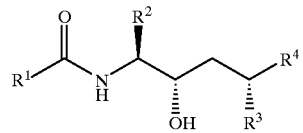

Ia wherein $R^1$, $R^2$, $R^3$, $R^4$ and $R^5$ are as described in claim 1.

3. A compound according to claim 1, wherein $R^1$ is optionally substituted quinoxalin-2-yl or quinoxalin-6-yl.

4. A compound according to claim 2, wherein $R^1$ is optionally substituted quinoxalin-2-yl or quinoxalin-6-yl.

5. A compound according to claim 1, wherein $R^2$ is optionally substituted benzyl.

6. A compound according to claim 2, wherein $R^2$ is optionally substituted benzyl.

7. A compound according to claim 3, wherein $R^2$ is optionally substituted benzyl.

8. A compound according to claim 4, wherein $R^2$ is optionally substituted benzyl.

9. A compound according to claim 1, wherein $R^3$ is optionally substituted $(C_1-C_{10})$alkyl or $(C_3-C_{10})$cycloalkyl-$(CH_2)_n$—.

10. A compound according to claim 2, wherein $R^3$ is optionally substituted $(C_1-C_{10})$alkyl or $(C_3-C_{10})$cycloalkyl-$(CH_2)_n$—.

11. A compound according to claim 4, wherein $R^3$ is optionally substituted $(C_1-C_{10})$alkyl or $(C_3-C_{10})$cycloalkyl-$(CH_2)_n$—.

12. A compound according to claim 3, wherein $R^3$ is optionally substituted $(C_1-C_{10})$alkyl or $(C_3-C_{10})$cycloalkyl-$(CH_2)_n$—.

13. A compound according to claim 1, wherein $R^3$ is optionally substituted n-butyl, t-butyl, isobutyl, n-pentyl, 2methyl-pentyl, cyclopentyl, or cyclohexl.

14. A compound according to claim 2, wherein $R^3$ is optionally substituted n-butyl, t-butyl, isobutyl, n-pentyl, 2-methyl-pentyl, cyclopentyl, or cyclohexyl.

15. A compound according to claim 6, wherein $R^3$ is optionally substituted n-butyl, t-butyl, isobutyl, n-pentyl, 2methyl-pentyl, cyclopentyl, or cyclohexyl.

16. A compound according to claim 3 wherein $R^3$ is optionally substituted n-butyl, t-butyl, isobutyl, n-pentyl, 2-methyl-pentyl, cyclopentyl, or cyclohexyl.

17. A compound according to claim 1, wherein $R^3$ is substituted by fluoro or hydroxy.

18. A compound according to claim 2, wherein $R^3$ is substituted by fluoro or hydroxy.

19. A compound according to claim 1, wherein $R^3$ is 4,4-difluoro-cyclohexylmethyl, 2-fluoro-2-methyl-butyl, isobutyl, or 1-hydroxy-cyclohexyl.

20. A compound according to claim 2, wherein $R^3$ is 4,4-difluoro-cyclohexylmethyl, 2-fluoro-2-methyl-butyl, isobutyl, or 1-hydroxy-cyclohexyl.

21. A compound according to claim 6, wherein $R^3$ is 4,4-difluoro-cyclohexylmethyl, 2-fluoro-2-methyl-butyl, isobutyl, or 1-hydroxy-cyclohexyl.

22. A compound according to claim 3 wherein $R^3$ is 4,4-difluoro-cyclohexylmethyl, 2-fluoro-2-methyl-butyl, isobutyl, or 1-hydroxy-cyclohexyl.

23. A compound according to claim 8 wherein $R^3$ is 4,4-difluoro-cyclohexylmethyl, 2-fluoro-2-methyl-butyl, isobutyl, or 1-hydroxy-cyclohexyl.

24. A compound according to claim 1, wherein said compound is:

Quinoxaline-2-carboxylic acid [1(S)-(3-fluoro-benzyl)-2(S),7-dihydroxy-4(R)-(1H-imidazol-2-yl)-7-methyl-octyl]-amide;

Quinoxaline-2-carboxylic acid [1(S)-benzyl-2(S),7-dihydroxy-4(R)-(1H-imidazol-2-yl)-7-methyl-octyl]-amide;

Quinoxaline-2-carboxylic acid [7-fluoro-1(S)-(3-fluoro-benzyl)-2(S)-hydroxy-4(R)-(1H-imidazol-2-yl)-7-methyl-octyl]-amide;

Quinoxaline-2-carboxylic acid [1(S)-benzyl-7-fluoro-2(S)-hydroxy-4(R)-(1H-imidazol-2-yl)-7-methyl-octyl]-amide;

Quinoxaline-2-carboxylic acid [1(S)-(3-fluoro-benzyl)-2(S),7-dihydroxy-7-methyl-4(R)-sulfamoyl-octyl]-amide;

Quinoxaline-2-carboxylic acid (1(S)-benzyl-2(S),7-dihydroxy-7-methyl-4(R)-sulfamoyl-octyl)-amide;

Quinoxaline-2-carboxylic acid [7-fluoro-1(S)-(3-fluoro-benzyl)-2(S),-hydroxy-7-methyl-4(R)-sulfamoyl-octyl]-amide;

Quinoxaline-2-carboxylic acid (1(S)-benzyl-7-fluoro-2(S)-hydroxy-7-methyl-4(R)-sulfamoyl-octyl)-amide;

Quinoxaline-2-carboxylic acid [1(S)-(3-fluoro-benzyl)-(2(S),7-dihydroxy-7-methyl-4(R)-methylsulfamoyl-octyl]-amide;

Quinoxaline-2-carboxylic acid (1(S)-benzyl-2(S)-7-dihydroxy-7-methyl-4(R)-methylsulfamoyl-octyl)-amide;

Quinoxaline-2-carboxylic acid [(S)-(3-fluoro-benzyl)-2(S),7-hydroxy-7-methyl-4(R)-methylsulfamoyl-octyl]-amide;

Quinoxaline-2-carboxylic acid [I(S)-benzyl-7-fluoro-2(S)-hydroxy-7-methyl-4(R)-methylsulfamoyl-octyl)-amide;

Quinoxaline-2-carboxylic acid [4(R)-(4-chloro-1H-imidazol-2-yl )-1(S)-(3-fluoro-benzyl)-2(S),-7-fluoro-benzyl)-2(S)-hydroxy-dihydroxy-7-methyl-octyl]-amide;

Quinoxaline-2-carboxylic acid [1(S)-benzyl-4(R)(4-chloro-1H-imidazol-2-yl)-2(S),-7-hydroxy-7-methyl-octyl]-amide;

Quinoxaline-2-carboxylic acid [4(R)-(4-chloro-1H-imidazol-2-yl)-7-fluoro-1(S)-(3-fluoro-benzyl)-2(S)-hydroxy-7-methyl-octyl]-amide;

Quinoxaline-2-carboxylic acid [1(S)-benzyl-4(R)(4-chloro-1H-imidazol-2-yl)-7-fluoro-2(S)-hydroxy-7-methyl-octyl]-amide;

Quinoxaline-2-carboxylic acid [1(S)-(3-fluoro-benzyl)-4(R)-(4-fluoro-1H-imidazol-2-yl)-2(S),7-dihydroxy-7-methyl-octyl]-amide;

Quinoxaline-2-carboxylic acid [1(S)-benzyl-4(R)-(4-fluoro-1H-imidazol-2-yl)-2(S)-7-dihydroxy-7-methyl-octyl]amide;

Quinoxaline-2-carboxylic acid [7-fluoro-1(S)-(3-fluoro-benzyl)-4(R)-(4-fluoro-1H-imidazol-2-yl)-2(S)-hydroxy-7-methyl-octyl]-amide; and Quinoxaline-2-carboxylic acid [1(S)-benzyl-7-fluoro-4(R)-(4-fluoro-1H-imidazol-2-yl)-2(S)-hydroxy-7-methyl-octyl]amide.

* * * * *